(12) United States Patent
Komarova et al.

(10) Patent No.: US 9,675,660 B2
(45) Date of Patent: Jun. 13, 2017

(54) PEPTIDES FOR INHIBITING ANGIOGENESIS

(71) Applicant: THE BOARD OF TRUSTEES OF THE UNIVERSITY OF ILLINOIS, Urbana, IL (US)

(72) Inventors: Yulia A. Komarova, Chicago, IL (US); Mark Rosenblatt, Chicago, IL (US); Asrar B. Malik, Hinsdale, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 15/058,938

(22) Filed: Mar. 2, 2016

(65) Prior Publication Data

US 2016/0256518 A1    Sep. 8, 2016

Related U.S. Application Data

(60) Provisional application No. 62/126,968, filed on Mar. 2, 2015.

(51) Int. Cl.

| | | |
|---|---|---|
| *A61K 38/00* | (2006.01) | |
| *A61K 38/08* | (2006.01) | |
| *A61K 38/10* | (2006.01) | |
| *C07K 14/515* | (2006.01) | |
| *A61B 3/10* | (2006.01) | |
| *A61F 9/008* | (2006.01) | |
| *A61K 45/06* | (2006.01) | |
| *A61B 3/12* | (2006.01) | |

(52) U.S. Cl.
CPC .............. *A61K 38/10* (2013.01); *A61B 3/102* (2013.01); *A61F 9/00821* (2013.01); *A61K 38/08* (2013.01); *A61K 45/06* (2013.01); *A61B 3/1241* (2013.01); *A61F 2009/00851* (2013.01); *A61F 2009/00863* (2013.01); *A61F 2009/00865* (2013.01); *A61F 2009/00872* (2013.01)

(58) Field of Classification Search
None
See application file for complete search history.

(56) References Cited

U.S. PATENT DOCUMENTS

| 4,554,101 | A | 11/1985 | Hopp |
| 8,912,139 | B2 | 12/2014 | Komarova et al. |
| 2008/0317773 | A1 | 12/2008 | Crisanti |
| 2009/0111754 | A1 | 4/2009 | Aggarwal et al. |
| 2010/0190691 | A1 | 7/2010 | Epenetos et al. |

FOREIGN PATENT DOCUMENTS

| WO | WO-2010/072943 A1 | 7/2010 |
| WO | WO-2012/042118 A2 | 6/2011 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Geyer et al., Microtubule-Associated Protein EB3 Regulates IP3 Receptor Clustering and Ca(2+) Signaling in Endothelial Cells, *Cell Rep*, 12(1):79-89 (2015).
Gong et al., Optimization of an Image-Guided Laser-Induced Choroidal Neovascularization Model in Mice, *PLoS One*, 10(7):e0132643 (2015).
Komarova et al., VE-cadherin signaling induces EB3 phosphorylation to suppress microtubule growth and assemble adherens junctions, *Molecular Cell*, 48(6):914-25 (2012).
Kyte et al., A simple method for displaying the hydropathic character of a protein, *J. Mol. Biol.*, 157:105-132 (1982).
Saqib et al., Structure-based design of inhibitory peptide for end binding proteins, *FASEB J.*, 26:1122.6 (2012).
The Merck Manual, Angioedema, (http://www.merckmanuals.com/professional/immunology-allergic-disorders/allergic,-autoimmune,-and-other-hypersensitivity-disorders/angioedema), copyright 2010-2014, accessed Aug. 20, 2014.
The Merck Manual, Anaphalaxis, (https://www.merckmanuals.com/professional/immunology-allergic-disorders/allergic,-autoimmune,-and-other-hypersensitivity-disorders/anaphylaxis ; accessed Jun. 9, 2015).
Uniprot Accession No. F2AQ33, LoIC/E family liprotein releasing system, transmembrane protein (2011).
Uniprot Accession No. A6H8K3, ITPR3 protein (2007).
UniProt sequence Q7UPK4, Probable lipoprotein releasing system transmembrane protein LoIC (2003).
WebMD (lung injury http://www.webmd.com/lung/lung-injuries, copyright 2005-2014, accessed Aug. 20, 2014).
International Search Report and Written Opinion of the International Searching Authority issued in connection with International Application No. PCT/US2012/042118, dated Dec. 14, 2012.
International Preliminary Report on Patentability, PCT/US2012/042118, dated Dec. 17, 2013.

* cited by examiner

Primary Examiner — Christine J Saoud
Assistant Examiner — Jon M Lockard
(74) Attorney, Agent, or Firm — Marshall, Gerstein & Borun LLP

(57) ABSTRACT

The present invention relates to peptides for inhibiting angiogenesis. The present invention also relates to methods of inhibiting angiogenesis and methods of treating disorders associated with VEGF-induced vascular permeability using the peptides of the invention.

18 Claims, 12 Drawing Sheets

```
IP₃R₁isoform1         VTPVKYARLWSEIPSEIAIDD
IP₃R₁isoform2         VTPVKYARLWSEIPSEIAIDD
         IP₃R₂         VVPVRYARLWTEIPTKITIHE
         IP₃R₃         VTPVKFARLWTEIPTAITIKD
    EB binding         --------S/TxIP--------
SEQ ID NO: 1 IP₃R₃ peptide    KFARLWTEIPTAIT
```

FIG. 2

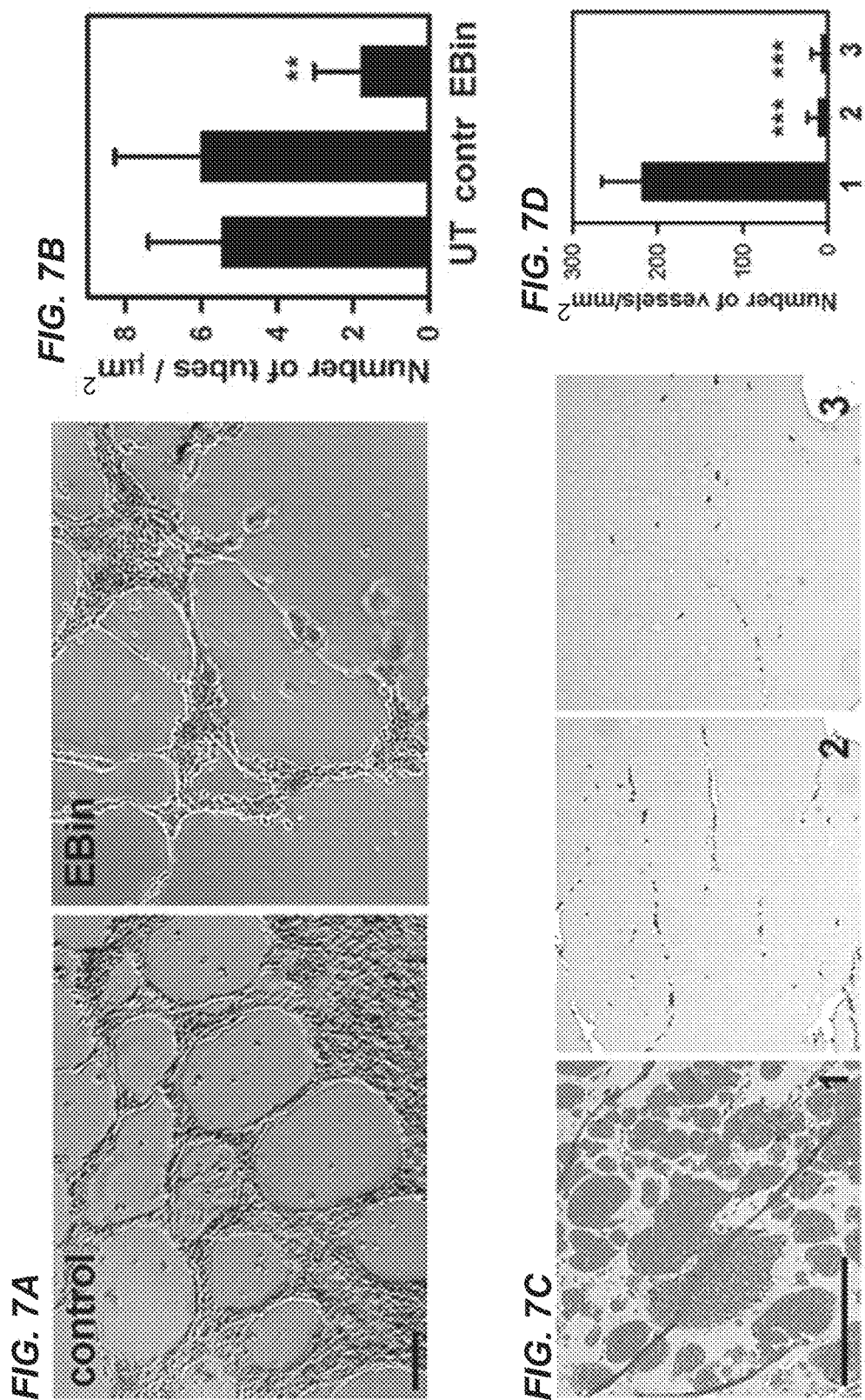

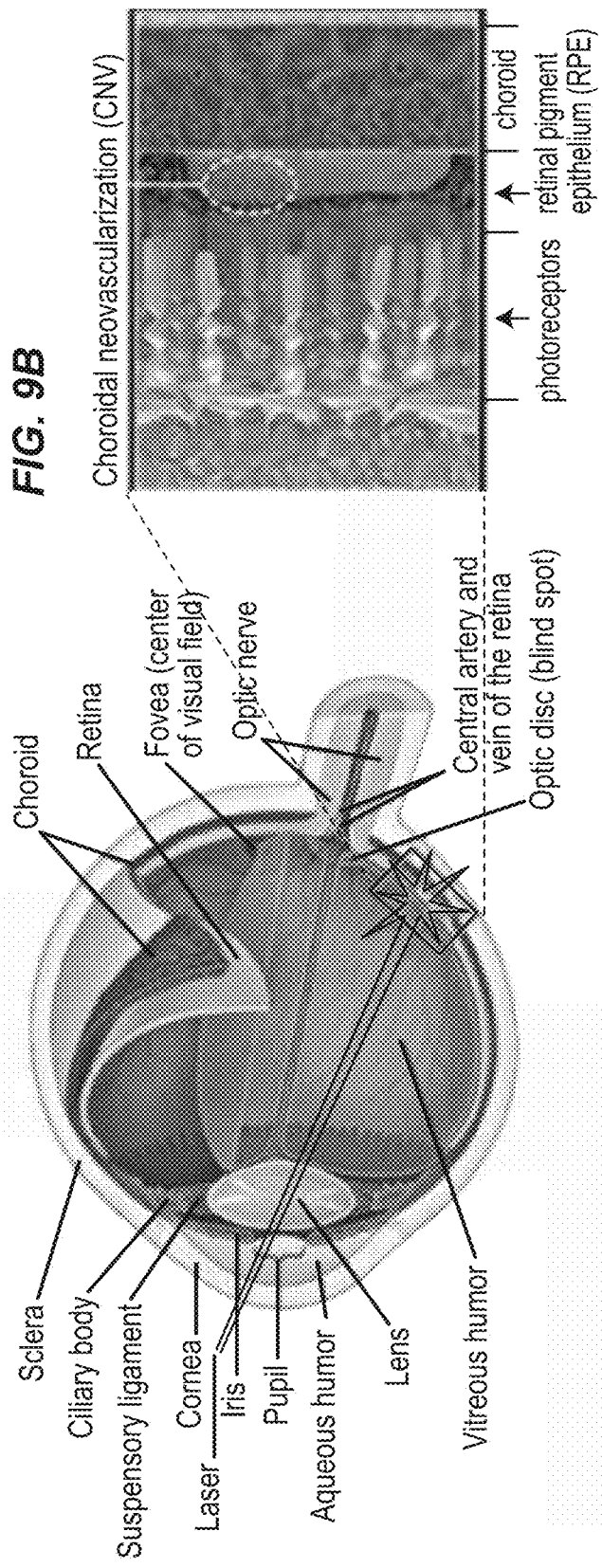
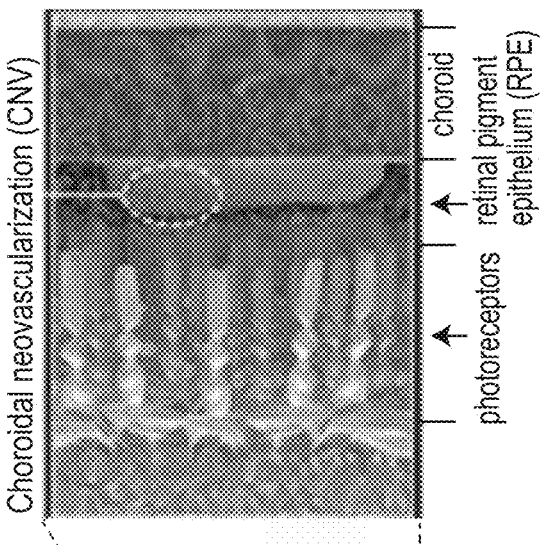
FIG. 9A
FIG. 9B

FIG. 11A
Control Peptide | EBIN | α-VEGF ab
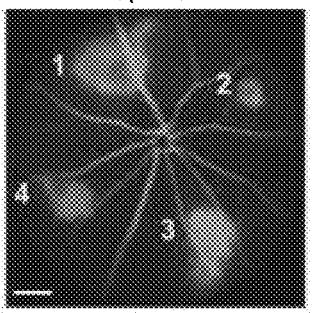 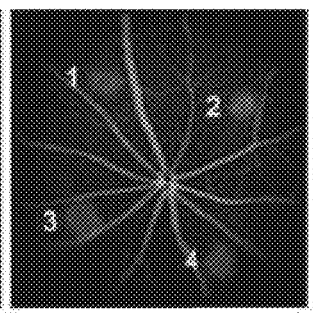 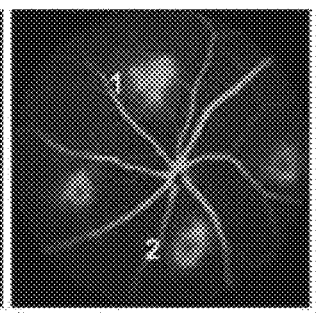
FIG. 11B
Control Peptide | EBIN | α-VEGF ab
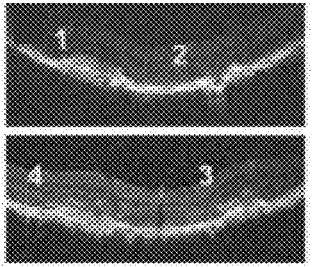 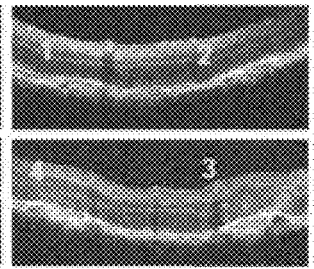 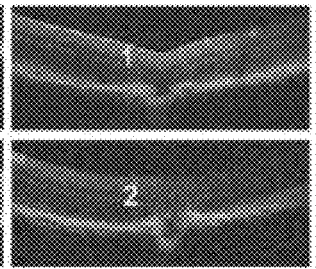
FIG. 11C
Control Peptide | EBIN | α-VEGF ab
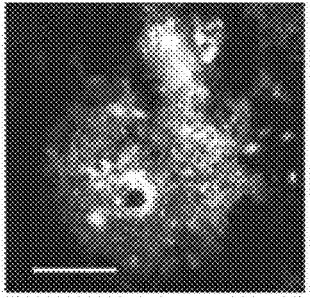 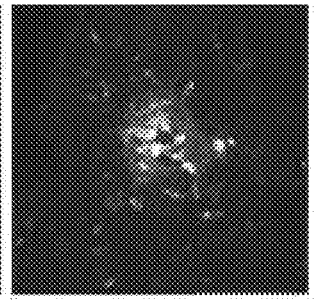 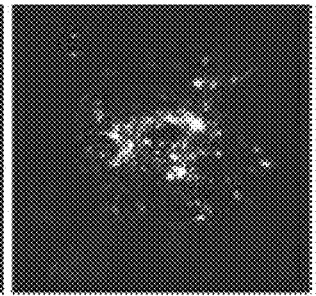
FIG. 11D
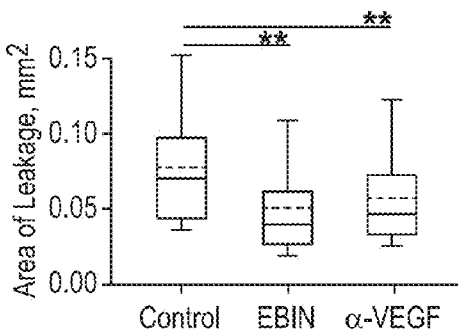
FIG. 11E
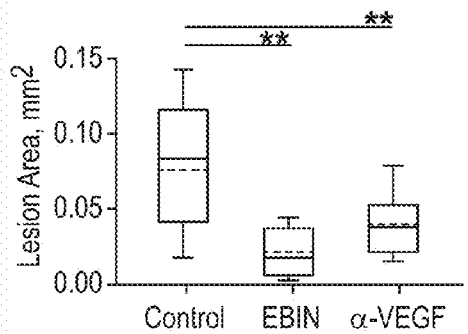

PEPTIDES FOR INHIBITING ANGIOGENESIS

This application claims priority to U.S. Provisional Patent Application No. 62/126,968 filed on Mar. 2, 2015, which is incorporated herein by reference in its entirety.

FIELD OF INVENTION

The present invention relates to peptides for inhibiting angiogenesis. The present invention also relates to methods of inhibiting angiogenesis and methods of treating disorders associated with VEGF-induced vascular permeability using the peptides of the invention.

BACKGROUND

Microtubule (MT) cytoskeleton provides an important control-point of endothelial barrier regulation; however, the role of this key cytoskeleton element has not been well studied. The MT stabilizing drug taxol has been shown to attenuate the endothelial vascular leakage in mice models of lung inflammation suggesting that MTs may be important in mediating increased lung vascular permeability. However, taxol displays a general toxicity that makes it an inconvenient drug for doctors and their patients.

Microtubule end binding proteins are highly conserved microtubule plus-end tracking accessory factors that bind to growing microtubules (MTs) and suppress MT catastrophic events. Two such end binding proteins, EB1 and EB3, play roles in regulating endothelial cytoskeletal dynamics and cell shape change, the primary determinants of the permeability of endothelial barrier.

$Ca^{2+}$ is a highly versatile second messenger that regulates endothelial permeability and vascular homeostasis. The activation of phospholipase C β(PLCβ), downstream of pro-inflammatory mediators promotes hydrolysis of phosphotidyl inositolbisphosphate (PIP2) into inositol 1,4,5-trisphosphate ($IP_3$) and diacylglycerol (DAG). $IP_3$ stimulates $Ca^{2+}$ release from $IP_3$-sensitive intracellular stores, i.e., the endoplasmic reticulum (ER). The depletion of $Ca^{2+}$ from ER stores is mediated by activation of $IP_3R$ on the ER membrane and leads to transient increase in intracellular $Ca^{2+}$. $Ca^{2+}$ entry or "influx" is mediated by transient receptor potential canonical (TRPC) channels that are permeable to various cations including $Ca^{2+}$ and $Mg^{2+}$. TRPC1 and 4 are store-operated $Ca^{2+}$ channels (SOC) in endothelial lung microvascular cells that are activated by depletion of ER.

The increase in intracellular concentration of $Ca^{2+}$ up-regulates activity of protein kinase Cα (PKC α). PKC α is a key regulator of the endothelial permeability response to multiple mediators including Vascular Endothelial Growth Factor (VEGF). PKC α phosphorylates p120-catenin and mediates its dissociation from VE-cadherin, thus resulting in VE-cadherin internalization PKC α also acts upstream of RhoA activation by phosphorylating p115RhoGEF and GDI-1. RhoA in turn facilitates phosphorylation-induced inhibition of myosin light chain phosphatase (MLCP) by activating Rho kinase (ROCK). The inhibition of MLCP is accompanied by the $Ca^{2+}$/calmodulin-dependent activation of MLCK that leads to phosphorylation of MLC and induces acto-myosin contraction in response to pro-inflammatory mediators such as thrombin and histamine and growth factors.

The integrity of MT cytoskeleton is required for $IP_3$-induced $Ca^{2+}$ release from ER stores. Alteration of MT dynamics by MT destabilizing or MT stabilizing agents nocodazole, colchicine and taxol inhibits $IP_3$-gated release of $Ca^{2+}$, suggesting that MT dynamics are required for full activation of $IP_3R$. The MT cytoskeleton is involved in remodeling of ER, thus ensuring organization and propagation of $Ca^{2+}$ waves in response to external stimuli. The ER attaches to and elongates together with MT growing ends though direct interaction of EB1 and EB3 with stromal interaction molecule 1 (STIM1). Depletion of EB1 in HeLa (HeLa cells do not express EB3) decreases ER protrusion events, however does not inhibit activation of SOC by thapsigargin suggesting that some other mechanisms are involved in activation of SOC and propogation of calcium signaling in epithelial cells. In endothelial cells, the localization of $IP_3R$ in caveolae is critical for both ER $Ca^{2+}$ store depletion and SOC activation. This indicates that activation of $IP_3R$ and/or its responsiveness to $IP_3$ is important element of calcium signaling. Consistent with previous findings, we found that MT cytoskeleton positively regulates $IP_3R$ activation in response to $IP_3$ and thus transmits extracellular signals throughout the cell, eliciting a physiological response. EB3 but not EB1 directly interacts with $IP_3Rs$ and this interaction provides a critical control point for organization of calcium signals in endothelial cells.

Vascular endothelial growth factor (VEGF) is known to contribute to angiogenesis via direct and indirect methods. VEGF is known to render the microvascular endothelial cells hyperpermeable so that the plasma proteins spill into the extravascular space, leading to clotting of extravasated fibrogen with deposition of a fibrin gel. The extravascular fibin serves as a matrix that supports the ingrowth of new blood vessels and other mesenchymal cells that generate mature, vascularized stroma. Thus, inhibition of VEGF-induced vascular permeability will result in inhibition of angiogenesis. Novel therapies are needed to prevent VEGF-induced vascular permeability and to inhibit angiogenesis.

The formation of tumor's network of blood vessels, i.e. neovascularization, plays an essential role throughout tumor development by helping the tumor to grow and metastasize. Once a tumor lesion exceeds a few millimeters in diameter, hypoxia and nutrient deprivation triggers an "angiogenic switch." Tumor cells release vascular endothelial growth factor (VEGF), which stimulates the sprouting and proliferation of endothelial cells. Several anti-angiogenic therapies are now approved by the FDA for cancer, including the humanized functional-blocking antibody fragment against VEGF-A, Avastin (bevacizumab) and the tyrosine kinase inhibitors, sorafenib and sunitinib, which target several growth receptors. Thus, therapies controlling tumor-associated angiogenesis are a promising tactic in limiting cancer progression and metastasis.

Loss of the inner endothelial blood-retinal barrier and the resultant macular edema and damage are the major causes of eye disorder and blindness in the elderly population. At present, these conditions, also known as age-related macular degeneration (AMD), are incurable. In addition, the neovascular form of AMD is characterized by growth of the blood vessels from the choroid, which penetrate through Bruch's membrane into the subretinal area. Some effective therapies to stem the common underlying cause of neovascular AMD are limited with the objective of hindering the vision loss by destroying new vessels arising in the choroid. Although current treatments with intravitreal injection of corticosteroids and anti-VEGF agents are effective in delaying progression of eye disease, they do not completely eliminate the risk of blindness. Therefore, novel and more potent therapies or combinational therapy approaches for treating eye disorders and preventing vision loss are needed.

SUMMARY OF INVENTION

Provided herein is an isolated peptide. The peptide may comprise KFARLWTEIPTAIT (SEQ ID NO: 1), FTEIPTI (SEQ ID NO: 3), a fragment thereof, or a variant thereof. The peptide may also consist of KFARLWTEIPTAIT (SEQ ID NO: 1), FTEIPTI (SEQ ID NO: 3), a fragment thereof, or a variant thereof. The variant may comprise a conservative substitution. The variant may comprise any peptide sequence containing Ser/Thr-x-Ile-Pro sequence (SEQ ID NO: 5), minimal EB binding consensus motif sequence. The peptide may be conjugated to a fatty acid, i.e. myristoylated or linked to a carrier peptide. The carrier peptide may be antennapedia peptide (AP), antennapedia peptide, penetratin peptide, TAT, tranportan or polyarginine. The peptide may be part of a pharmaceutical formulation, which may include a pharmaceutically acceptable excipient.

The invention provides for methods of inhibiting angiogenesis comprising administering to a patient in need thereof an isolated peptide comprising the amino acid sequence of KFARLWTEIPTAIT (SEQ ID NO:1), FTEIPTI (SEQ ID NO: 3) or a fragments thereof. The methods include administering a therapeutically effective amount of a peptide of the invention, such as an amount effective to inhibit angiogenesis. In addition, the methods include administering pharmaceutical compositions comprising a therapeutically effective amount of a peptide of the invention. The invention provides for a method of treatment in which the patient in need is suffering from cancer or a disorder associated with VEGF-induced permeability, such as visual impairment or vision loss (blindness), macular degeneration, central retinal vein occlusion, branch retinal venin occlusion proliferative diabetic retinopathy, neovascular age-related macular degeneration (AMD), retinopathy of prematurity, ischemic retinopathy, intraocular neovascularization, corneal neovascularization, retinal neovascularization, choroidal neovascularization, diabetic macular edema, diabetic retina ischemia, diabetic retinal edema, and proliferative diabetic retinopathy, rubeosis iridis, neovascular glaucoma, retinoblastoma, uveitis and corneal graft neovascularization.

The invention also provides for methods of treating a disorder associated with VEGF-induced vascular permeability comprising administering to a patient in need thereof an isolated peptide comprising the amino acid sequence of KFARLWTEIPTAIT (SEQ ID NO:1), FTEIPTI (SEQ ID NO: 3) or a fragments thereof. The methods include administering a therapeutically effective amount of a peptide of the invention, such as an amount effective to inhibit VEGF-induced vascular permeability. In addition, the methods include administering pharmaceutical compositions comprising a therapeutically effective amount of a peptide of the invention. The invention provides for a method of treatment in which the patient in need is suffering from cancer or a disorder associated with VEGF-induced permeability, such as visual impairment or vision loss (blindness), macular degeneration, central retinal vein occlusion, branch retinal venin occlusion proliferative diabetic retinopathy, neovascular age-related macular degeneration (AMD), retinopathy of prematurity, ischemic retinopathy, intraocular neovascularization, corneal neovascularization, retinal neovascularization, choroidal neovascularization, diabetic macular edema, diabetic retina ischemia, diabetic retinal edema, and proliferative diabetic retinopathy, rubeosis iridis, neovascular glaucoma, retinoblastoma, uveitis and corneal graft neovascularization.

In any of the foregoing methods, the peptide administered may be linked to a carrier peptide such as antennapedia peptide (AP), antennapedia peptide, penetratin peptide, TAT, tranportan or polyarginine. In addition, in any of the foregoing methods, the peptide administered may be conjugated to a fatty acid, e.g. myristoylated.

In any of the foregoing a methods, the isolated peptide comprising the amino acid sequence of KFARLWTEIPTAIT (SEQ ID NO:1), FTEIPTI (SEQ ID NO: 3) or a fragments thereof is administered in combination with one or more VEGF inhibitors, wherein "VEGF inhibitors" refer to anti-VEGF antibodies and fragments thereof, anti-VEGF receptor (anti-VEGFR) antibodies and fragments thereof, antagonistic peptides and small molecules which inhibit the activity or signaling pathway of VEGF and/or VEGFR. Exemplary VEGF inhibitors include Bevacizumab (Avastin), Ranibizumab (Lucentis), Pegaptanib (Macugen), Aflibercept (Eylea), Sorafenib (Nexvar), Sunitinib (Sutent), Pazopanib (Votrient), Axitinib (Inlyta), PTK787/ZK222584, ZD-6474, SU6668, PD-547,632, VEGF-Trap, CEP-7055, NM-3, or SU11248.

In any of the foregoing methods of the invention, the isolated peptide comprising the amino acid sequence of KFARLWTEIPTAIT (SEQ ID NO:1), FTEIPTI (SEQ ID NO: 3) or a fragments thereof may be administered in combination with laser treatment for eye disease, wherein "eye disease" refers to visual impairment or vision loss (blindness), macular degeneration, central retinal vein occlusion, branch retinal venin occlusion proliferative diabetic retinopathy, neovascular age-related macular degeneration (AMD), retinopathy of prematurity, ischemic retinopathy, intraocular neovascularization, corneal neovascularization, retinal neovascularization, choroidal neovascularization, diabetic macular edema, diabetic retina ischemia, diabetic retinal edema, and proliferative diabetic retinopathy, rubeosis iridis, neovascular glaucoma, retinoblastoma, uveitis and corneal graft neovascularization.

In any of the foregoing methods of the invention, the isolated peptide comprising the amino acid sequence of KFARLWTEIPTAIT (SEQ ID NO: 1), FTEIPTI (SEQ ID NO: 3) or a fragments thereof may be administered in combination with a steroid or any current method treatment for eye disease.

In addition, in any of the methods of the invention, the isolated peptide of the invention, VEGF inhibitor, steroid or any other treatment may be administered by intravitreal injection or topically such as in the form of an eye drop.

The invention also provides for an use of an isolated peptide for the preparation of a medicament for the inhibition of angiogenesis in a patient in need, wherein the peptide comprises the amino acid sequence of KFARLWTEIPTAIT (SEQ ID NO: 1), FTEIPTI (SEQ ID NO: 3) or a fragments thereof. The uses of the invention include use of the isolated peptide of the invention for the preparation of a medicament comprising a therapeutically effective amount of a peptide of the invention, such as an amount effective to inhibit angiogenesis. In addition, the invention provides for us of the isolated peptide of the invention for the preparation of a medicament comprising a composition comprising a therapeutically effective amount of a peptide of the invention. The invention provides use of the isolated peptide of the invention for the preparation of a medicament to administer to a suffering from cancer or a disorder associated with VEGF-induced permeability, such as visual impairment or vision loss (blindness), macular degeneration, central retinal vein occlusion, branch retinal venin occlusion proliferative diabetic retinopathy, neovascular age-related macular degeneration (AMD), retinopathy of prematurity, ischemic retinopathy, intraocular neovascularization, corneal neovascularization, retinal neovascularization, choroidal neovascularization, diabetic macular edema, diabetic retina ischemia, diabetic retinal edema, and proliferative diabetic retinopathy, rubeosis iridis, neovascular glaucoma, retinoblastoma, uveitis and corneal graft neovascularization.

The invention also provides for the use of an isolated peptide for the preparation of a medicament for the treatment of a VEGF-induced vascular disorder, wherein the peptide comprises the amino acid sequence of KFARLWTEIPTAIT (SEQ ID NO: 1), FTEIPTI (SEQ ID NO: 3) or a fragments thereof. The uses of the invention include use of the isolated peptide of the invention for the preparation of a medicament comprising a therapeutically effective amount of a peptide of the invention, such as an amount effective to inhibit VEGF-induced vascular permeability. In addition, the invention provides for us of the isolated peptide of the invention for the preparation of a medicament comprising a composition comprising a therapeutically effective amount of a peptide of the invention. The invention provides for use of the peptide of the invention for the preparation of a medicament to administer to a subject suffering from cancer or a disorder associated with VEGF-induced permeability, such as visual impairment or vision loss (blindness), macular degeneration, central retinal vein occlusion, branch retinal venin occlusion proliferative diabetic retinopathy, neovascular age-related macular degeneration (AMD), retinopathy of prematurity, ischemic retinopathy, intraocular neovascularization, corneal neovascularization, retinal neovascularization, choroidal neovascularization, diabetic macular edema, diabetic retina ischemia, diabetic retinal edema, and proliferative diabetic retinopathy, rubeosis iridis, neovascular glaucoma, retinoblastoma, uveitis and corneal graft neovascularization.

In any of the foregoing uses of the invention, the isolated peptide administered may be linked to a carrier peptide such as antennapedia peptide (AP), antennapedia peptide, penetratin peptide, TAT, tranportan or polyarginine. In addition, in any of the foregoing methods, the isolated peptide administered may be conjugated to a fatty acid, e.g. myristoylated.

In any of the foregoing uses, the isolated peptide comprising the amino acid sequence of KFARLWTEIPTAIT (SEQ ID NO: 1), FTEIPTI (SEQ ID NO: 3) or a fragments thereof is administered in combination with one or more VEGF inhibitors, wherein "VEGF inhibitors" refer to anti-VEGF antibodies and fragments thereof, anti-VEGFR antibodies and fragments thereof, antagonistic peptides and small molecules which inhibit the activity or signaling pathway of VEGF or VEGFR. Exemplary VEGF inhibitors include Bevacizumab (Avastin), Ranibizumab (Lucentis), Pegaptanib (Macugen), Aflibercept (Eylea), Sorafenib (Nexvar), Sunitinib (Sutent), Pazopanib (Votrient), Axitinib (Inlyta), PTK787/ZK222584, ZD-6474, SU6668, PD-547,632, VEGF-Trap, CEP-7055, NM-3, or SU11248.

In any of the foregoing uses of the invention, the medicament comprising the amino acid sequence of KFARLWTEIPTAIT (SEQ ID NO:1), FTEIPTI (SEQ ID NO: 3) or fragments thereof may be administered in combination with laser treatment for eye disease, wherein "eye disease" refers to visual impairment or vision loss (blindness), macular degeneration, central retinal vein occlusion, branch retinal venin occlusion proliferative diabetic retinopathy, neovascular age-related macular degeneration (AMD), retinopathy of prematurity, ischemic retinopathy, intraocular neovascularization, corneal neovascularization, retinal neovascularization, choroidal neovascularization, diabetic macular edema, diabetic retina ischemia, diabetic retinal edema, and proliferative diabetic retinopathy, rubeosis iridis, neovascular glaucoma, retinoblastoma, uveitis and corneal graft neovascularization.

In any of the foregoing uses of the invention, the medicament may be administered in combination with a steroid or any current method of treatment for eye disease.

In addition, in any of the uses of the invention, the medicament may be administered by intravitreal injection or topically such as in the form of an eye drop.

The invention provides for an isolated peptide for the inhibition of angiogenesis, wherein the peptide comprises the amino acid sequence of KFARLWTEIPTAIT (SEQ ID NO: 1), FTEIPTI (SEQ ID NO: 3) or a fragments thereof.

The invention also provides for a composition comprising a therapeutically effective amount of a peptide of the invention for the inhibition of angiogenesis. The invention provides for an isolated peptide or a composition comprising a therapeutically effective amount of the peptide for inhibition of angiogenesis in a subject a suffering from cancer or a disorder associated with VEGF-induced permeability, such as visual impairment or vision loss (blindness), macular degeneration, central retinal vein occlusion, branch retinal venin occlusion proliferative diabetic retinopathy, neovascular age-related macular degeneration (AMD), retinopathy of prematurity, ischemic retinopathy, intraocular neovascularization, corneal neovascularization, retinal neovascularization, choroidal neovascularization, diabetic macular edema, diabetic retina ischemia, diabetic retinal edema, and proliferative diabetic retinopathy, rubeosis iridis, neovascular glaucoma, retinoblastoma, uveitis and corneal graft neovascularization.

The invention also provides for an isolated peptide for use in inhibition of angiogenesis in a patient suffering from a disorder associated with VEGF-induced vascular permeability wherein the isolated peptide comprises the amino acid sequence of KFARLWTEIPTAIT (SEQ ID NO:1), FTEIPTI (SEQ ID NO: 3) or a fragments thereof.

The invention also provide for a composition comprising a therapeutically effective amount of an isolated peptide of the invention for the inhibition of VEGF-induced vascular permeability. The invention provides for an isolated peptide or a composition comprising a therapeutically effective amount of the peptide for inhibition of VEGF-induced permeability in a subject a suffering from cancer or a disorder associated with VEGF-induced permeability, such as visual impairment or vision loss (blindness), macular degeneration, central retinal vein occlusion, branch retinal venin occlusion proliferative diabetic retinopathy, neovascular age-related macular degeneration (AMD), retinopathy of prematurity, ischemic retinopathy, intraocular neovascularization, corneal neovascularization, retinal neovascularization, choroidal neovascularization, diabetic macular edema, diabetic retina ischemia, diabetic retinal edema, and proliferative diabetic retinopathy, rubeosis iridis, neovascular glaucoma, retinoblastoma, uveitis and corneal graft neovascularization.

The invention also provides for an isolated peptide for the treatment for a disorder associated with VEGF-induced vascular permeability. For example, the VEGF associated vascular disorder is visual impairment or vision loss (blindness), macular degeneration, central retinal vein occlusion, branch retinal venin occlusion proliferative diabetic retinopathy, neovascular age-related macular degeneration (AMD), retinopathy of prematurity, ischemic retinopathy, intraocular neovascularization, corneal neovascularization, retinal neovascularization, choroidal neovascularization, diabetic macular edema, diabetic retina ischemia, diabetic retinal edema, and proliferative diabetic retinopathy, rubeosis iridis, neovascular glaucoma, retinoblastoma, uveitis and corneal graft neovascularization.

Any of the peptides of the invention are used for inhibiting angiogenesis or for treating a disorder associated with VEGF-induced vascular permeability may be linked to a carrier peptide such as antennapedia peptide (AP), antennapedia peptide, penetratin peptide, TAT, tranportan or polyarginine. In addition, any of the isolated peptides of the invention for use in inhibiting angiogenesis or treating a disorder associated with VEGF-induced vascular permeability may be conjugated to a fatty acid, e.g. myristoylated.

Any of the isolated peptides or compositions of the invention may be administered in combination with one or more VEGF inhibitors, wherein "VEGF inhbitors" refer to s anti-VEGF antibodies and fragments thereof, anti-VEGFR antibodies and fragments thereof, antagonistic peptides and small molecules that inhibit the activity or signaling pathway of VEGF or VEGFR. Exemplary VEGF inhibitors include Bevacizumab (Avastin), Ranibizumab (Lucentis), Pegaptanib (Macugen), Aflibercept (Eylea), Sorafenib (Nexvar), Sunitinib (Sutent), Pazopanib (Votrient), Axitinib (Inlyta), PTK787/ZK222584, ZD-6474, SU6668, PD-547,632, VEGF-Trap, CEP-7055, NM-3, or SU11248. In addition, the peptide or the VEGFR is administered by intravitreal injection or topically such as in the form of an eye drop.

Any of the isolated peptides or compositions of the invention may be administered in combination with laser treatment for eye disease wherein "eye disease" refers to visual impairment or vision loss (blindness), macular degeneration, central retinal vein occlusion, branch retinal venin occlusion proliferative diabetic retinopathy, neovascular age-related macular degeneration (AMD), retinopathy of prematurity, ischemic retinopathy, intraocular neovascularization, corneal neovascularization, retinal neovascularization, choroidal neovascularization, diabetic macular edema, diabetic retina ischemia, diabetic retinal edema, and proliferative diabetic retinopathy, rubeosis iridis, neovascular glaucoma, retinoblastoma, uveitis and corneal graft neovascularization.

The isolated peptides or compositions of the invention may be administered in combination with a steroid or any current method treatment for eye disease.

In addition, the isolated peptides or compositions of the invention may be administered by intravitreal injection or topically such as in the form of an eye drop.

BRIEF DESCRIPTION OF DRAWING

FIG. 2 shows an alignment of human $IP_3$ receptors (794-814 aa of $IP_3R_3$ type 3) with EB binding motif (highlighted). The $IP_3R_3$ peptide (SEQ ID NO: 1) is shown below the alignment.

(FIG. 4A) HMVECs pre-treated with AP-attached $IP_3R_3$ peptide or control (AP) peptide were loaded with Fura 2-AM and 340/380 ratio was calculated after stimulation of cells with thrombin (50 nM) in the absence and in the presence of extracellular $Ca^{2+}$. Arrow, time of thrombin addition. (FIG. 4B) Plot shows the mean ±SD for thrombin-induced $Ca^{2+}$ release and entry calculated as a maximum increase over the basal value. The increase is normalized to control non-treated cells from the same experiment (n=4).

FIG. 6A shows subcuteanous vascular leakage of albumin-bound Evans Blue Dye, which was induced by intradermal injection of VEGF, and FIG. 6B quantifies the vascular leakage as measured spectrophotometrically at 620 nm.

FIG. 7A-7D: FIG. 7A shows that EBIN inhibited tubulogenesis in matrigel coated wells (scale bar 200 μm). FIG. 7B shows the number of branches per area; UT=untreated; Contr=control peptide; $p<0.001$ (n=3 wells per group). FIG. 7C shows hemematoxylin and eosin (HE) staining of in vivo matrigel plugs. Group 1 was treated with control peptide and group 3 was treated with Myr-EBIN at 0, 36 and 60 hrs; group 2 received only 36 and 60 hour treatment. FIG. 7D shows the number of vessels per $mm^2$; *$p<0.001$ (n=15 per group). Scale bar, 200 μm.

FIG. 8A plots tumor growth curve in xenograft model; mean is shown; n=8 mice per group. FIG. 8B plots the number of vessels per area counted outside of the tumor; n=25 fields/mouse; N=5 mice; *, $p<0.05$; **, $p<0.01$.

FIG. 9A-9B shows an overview of the animal model for choroidal neovascularization (CNV) induction in: (FIG. 9A) Cross section view of the eye demonstrating the laser beam focused on pigment epithelium of retina to induce laser burn and rupture of Bruch's membrane, (FIG. 9B) Rupture of Bruch's membrane induces proliferation of blood vessel in choroid and CNV lesion into retina.

FIG. 11A-11E show the effect of EBIN treatment on CNV. Correlative analysis of vascular leakage (FIG. 11A) and lesion (FIG. 11B-FIG. 11C) in mice treated by intravitreal injection of control peptide (Myr-FAEIPTI), EBIN (Myr-FTEIPTI) and mouse anti-VEGF antibody (LEAF™). Representative images of Fundus Fluorescein Angiography (FIG. 11A) and corresponding Optical Coherence Tomography (FIG. 11B) at day 15 after laser photocoagulation; numbers in yellow indicate corresponding CNV lesions. Area of leakage correlates with the lesion size. (FIG. 11C) CNV lesion is detected by staining for isolectin B4 using flat-mount of retinal pigment epithelium/choroid/sclera. Quantification of the area of fluorescein leakage (FIG. 11D) and lesion (FIG. 11E) using images shown in (FIG. 11A) and (FIG. 11C); n=6-9 mice per group; **, $p<0.01$. Scale bar, 200 μm and 100 μm in (FIG. 11A) and (FIG. 11C), respectively. Comparison between groups were performed using ANOVA. Anti-VEGF treatment significantly altered wound healing/scaring of damaged area whereas treatment with EBIN did not affect healing process.

FIG. 12A shows the effects of 7-days acute toxicity study for EBIN. Representative images of Fundus Fluorescein Angiography F and corresponding Optical Coherence Tomography (FIG. 12B) at day 8 of intravitreal treatment with EBIN (1 μg/eye). Note, EBIN forms small crystals/precipitates inside of various humor; no visible changes in retinal vasculature and retinal pigment epithelium, choroid, sclera were detected.

DETAILED DESCRIPTION

Figure 1:
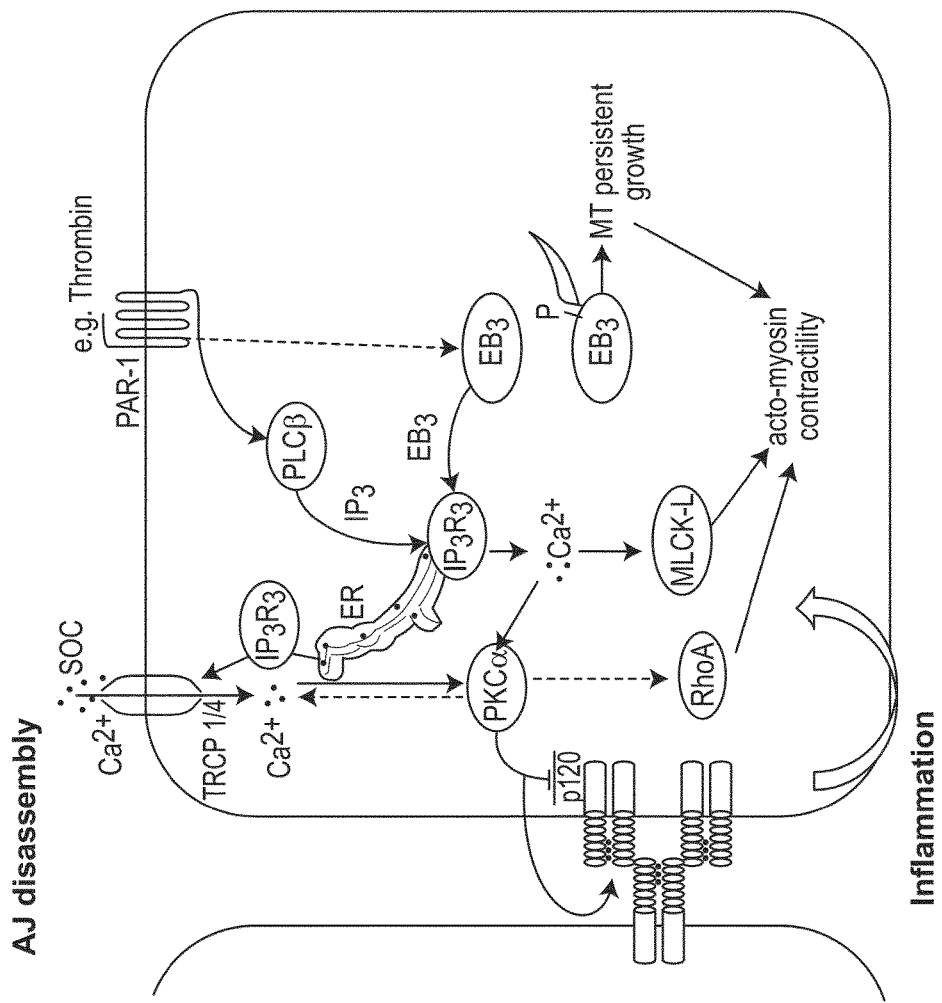
FIG. 1 shows the role of EB3 in inflammatory-induced hyper-permeability of endothelial barrier. EB3 establishes transient interactions of growing MT ends with the $IP_3R_3$, sensitizes the $IP_3R_3$ and positively regulates both $Ca^{2+}$ release from stores and SOC-dependent $Ca^{2+}$ entry during inflammation. This results in amplification of $Ca^{2+}$ signaling and increased permeability through PKCα-mediated phosphorylation of p120-catenin and acto-myosin contractility.

The inventors have made the surprising discovery that peptides derived from the EB3-interacting domain of inositol 1,4,5-trisphosphate ($IP_3$) receptor type 3 ($IP_3R_3$) reduce the interaction between End Binding Protein 3 (EB3) and $IP_3R_3$ and inhibit VEGF-induced vascular permeability or VEGF-induced microvascular leakage. The peptides of the invention demonstrate barrier-protective properties in various inflammatory diseases and demonstrate anti-angiogenic properties in vitro and in vivo.

Previous work suggested by the role of the MT cytoskeleton in regulating $IP_3$-gated release of $Ca^{2+}$ from ER store and EB3 is requires for ER $Ca^{2+}$ depletion. $IP_3R_3$ contains EB binding consensus motif, Ser/Thr-x-Ile-Pro (SxIP) (SEQ ID NO: 5). A short peptide based on $IP_3R_3$ sequence (KFARLWTEIPTAIT—SEQ ID NO: 1) shows high binding activity for EB3 (see Example 1). These studies demonstrate that the interaction between $IP_3R_3$ and EB3 critical in the mechanism of $IP_3R$ activation.

The role of EB3 in inflammatory-induced hyperpermeability of endothelial barrier centers on its ability to establish transient interactions of growing MT ends with $IP_3R_3$. As a result EB3 sensitizes $IP_3R_3$ to $IP_3$ and positively regulates $Ca^{2+}$ release from the endoplasmic reticulum (ER). This leads to SOC-dependent $Ca^{2+}$ entry and amplification of $Ca^{2+}$ signaling. Increased concentration of cytosolic $Ca^{2+}$ induces PKC α-mediated phosphorylation of p120-catenin resulting in disassembly of VE-cadherin adhesions. It also facilitates RhoA-dependent acto-myosin contractility resulting in the cell shape changes. See FIG. 1. This work is described in detail in International Application No. PCT/US2012/042118 and U.S. Pat. No. 8,912,139, which are incorporated by reference in their entirety.

The methods and materials described below prevent or inhibit VEGF-induced microvascular leakage and, therefore, are useful in inhibiting angiogenesis and treating disorders such as macular degeneration, diabetic retinopathy, cancer, central retinal vein occlusion and branch retinal venin occlusion, to name a few.

Definitions

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

"Angiogenesis" as used herein, refers to the process through which new blood vessels form from pre-existing vessels. For example, cytokines and extracellular matrix proteases induce tissue remodeling in preparation for migration of endothelial cells from existing vessels to form new vessels.

"Fragment" as used herein may mean a portion of a reference peptide or polypeptide or nucleic acid sequence.

"Identical" or "identity" as used herein in the context of two or more polypeptide or nucleotide sequences, may mean that the sequences have a specified percentage of residues or nucleotides that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation.

"Peptide" or "polypeptide" as used herein, may refer to a linked sequence of amino acids and may be natural, synthetic, or a modification or combination of natural and synthetic.

"Substantially identical," as used herein may mean that a first and second protein or nucleotide sequence are at least 50%-99% identical over a region of 6-100 or more amino acids nucleotides.

"Treating," "treatment," or "to treat" each may mean to alleviate, suppress, repress, eliminate, prevent or slow the appearance of symptoms, clinical signs, or underlying pathology of a condition or disorder on a temporary or permanent basis. Preventing a condition or disorder involves administering a agent of the present invention to a subject prior to onset of the disease. Suppressing a condition or disorder involves administering a agent of the present invention to a subject after induction of the condition or disorder but before its clinical appearance. Repressing the condition or disorder involves administering a agent of the present invention to a subject after clinical appearance of the disease.

The term "therapeutically effective" depends on the condition of a subject and the specific compound administered. The term refers to an amount effective to achieve a desired clinical effect. A therapeutically effective amount varies with the nature of the condition being treated, the length of time that activity is desired, and the age and the condition of the subject, and ultimately is determined by the health care provider. In one aspect, a therapeutically effective amount of a peptide or composition is an amount effective to inhibit, reduce or prevent VEGF-induced vascular permeability and/or angiogenesis.

A "variant" means a peptide or polypeptide that differs in amino acid sequence by the insertion, deletion, or conservative substitution of amino acids, but retains at least one biological activity. Representative examples of "biological activity" include the ability to bind to End Binding protein, a toll-like receptor (TLR) and to be bound by a specific antibody. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Provided herein is a peptide, which may comprise the amino acid sequence KFARLWTEIPTAIT (SEQ ID NO: 1), KFARLWAEIPTAIT (SEQ ID NO: 2) (also referred to herein as IP$_3$R$_3$ Peptide), FTEIPTI (SEQ ID NO: 3) (also referred to herein as End Binding Inhibitory Peptide, or "EBIN"), a peptide disclosed in Table 1 herein, a fragment thereof, or a variant thereof. The variant may comprise a conservative substitution. The peptide may comprise an EB binding consensus motif sequence, such as the EB binding consensus sequence of IP$_3$R$_3$, or a fragment thereof. The EB binding consensus sequence of IP$_3$R$_3$ may be Ser/Thr-x-Ile-Pro (SEQ ID NO: 5). The peptide may consist of KFARLWTEIPTAIT (SEQ ID NO: 1), KFARLWAEIPTAIT (SEQ ID NO:2), FTEIPTI (SEQ ID NO: 3), a consensus sequence comprising Ser/Thr-x-Ile-Pro (SEQ ID NO: 5), a peptide disclosed in Table 1 herein, a fragment of the foregoing, or a conservative variant of the foregoing. The variant may comprise any peptide sequence containing Ser/Thr-x-Ile-Pro sequence (SEQ ID NO: 5), minimal EB binding consensus motif sequence.

The peptide may comprise the amino acid sequence of KFARLWTEIPTAIT (SEQ ID NO: 1), KFARLWAEIPTAIT (SEQ ID NO:2) (also referred to herein as IP$_3$R$_3$ Peptide), FTEIPTI (SEQ ID NO: 3) (also referred to herein as End Binding Inhibitory Peptide, or "EBIN"), a peptide disclosed in Table 1 herein, a fragment thereof, or a variant thereof, wherein the peptide or a polypeptide comprising the peptide is 7 amino acid residues, 8 amino acid residues, 9, amino acid residues, 10, amino acid residues, 11, amino acid residues, 12 amino acid residues, 13 amino acid residues, 14 amino acid residues, 15 amino acid residues, 16 amino acid residues, 17 amino acid residues, 18 amino acid residues, 19, amino acid residues, 20 amino acid residues, 21 amino acid residues, 22 amino acid residues, 23 amino acid residues, 24 amino acid residues, 25 amino acid residues, 26 amino acid residues, 27 amino acid residues, 28 amino acid residues, 29 amino acid residues, 30 amino acid residues, 35 amino acid residues, 40 amino acid residues, 45 amino acid residues, 50 amino acid residues, 55 amino acid residues, 60 amino acid residues, 65 amino acid residues, 70 amino acid residues, 75 amino acid residues, 80 amino acid residues, 85 amino acid residues, 90 amino acid residues, 95 amino acid residues or 100 amino acid residues.

The peptide may be modified in that the amino acid sequence has one or more amino acid substitutions, amino acid insertions, amino acid deletions, carboxy terminal truncation, or an amino terminal truncation.

The peptide might also be glycosylated, phosphorylated, sulfated, glycosylated, animated, carboxylated, acetylated. For example, the C-terminal may be modified with amidation, addition of peptide alcohols and aldehydes, addition of esters, addition of p-nitorailine and thioesteres and multipelantigens peptides. The N-terminal and side chains may be modified by PEGylation, acetylation, formylation, addition of a fatty acid, addition of benzoyl, addition of bromoacetyl, addition of pyroglutamyl, succinylation, addition of tetrabutyoxycarbonyl and addition of 3-mercaptopropyl, acylations (e.g. lipopeptides), biotinylation, phosphorylation, sulfation, glycosylation, introduction of maleimido group, chelating moieties, chromophores and flurophores.

The peptide may be conjugated to a fatty acid, e.g. the peptide is myristoylated. For example, a fatty acid may be conjugated to the N-terminus of the peptide, such fatty acids include caprylic acid (C8), capric acid (C10), lauric acid (C12), myristic acid (C14), palmitic acid (C16) or stearic acid (C18) etc. Furthermore cysteines in peptides can be palmitoylated.

The peptide may be conjugated or linked to another peptide, such as a carrier peptide. The carrier peptide may facilitate cell-penetration, such as antennapedia peptide, penetratin peptide, TAT, tranportan or polyarginine.

The peptides may be cyclic. The peptide disclosed herein may be cyclized by adding a single or multiple disulfide bridges, adding a single or multiple amide bonds between the N- and C-terminus, heat to tail cyclization, side chain cyclization (e.g. lactam bridge, thioester), hydrocarbon-stabled peptides.

The peptide may be labeled with heavy isotope labeling, e.g. $^{15}$N, $^{13}$C, FITC, conjugation to a carrier protein, conjugation to imaging agent, FRET substrates with a flurophore/quencher pair, peptide-DNA conjugation, peptide-RNA conjugation and peptide-enzyme labeling.

The peptide may be within a fusion protein such as fused to a polypeptide or peptide which promotes oligomerization, such as a leucine zipper domain; a polypeptide or peptide which increases stability or to increase half-life, such as an immunoglobulin constant region; and a polypeptide which has a therapeutic activity different from peptide or the invention, a chemotherapeutic agent, an antibody or protein for tissue specific targeting, Fusions can be made either at the amino terminus or at the carboxy terminus of the polypeptide. The fusion proteins may be direct with no linker or adapter molecule or indirect using a linker or adapter molecule. A linker or adapter molecule may be one or more amino acid residues, typically up to about 20 to about 50 amino acid residues. A linker or adapter molecule may also be designed with a cleavage site for a protease to allow for the separation of the fused moieties. For example, the peptide may be fused to one or more domains of an Fc region of human IgG to increase the half-life of the peptide or the addition of a Fab variable domain to shorten the half-life of the peptide.

Methods of Treatment

Provided herein is a method of inhibiting, preventing or reducing angiogenesis. Angiogeneis is associated with tumor growth, cancer progression and metastasis, blindness and macular degeneration, diabetic retinopathy, to name a few.

The invention provides for method of inhibiting angiogenesis involved in tumor growth, cancer progression and metastasis. The invention also provides for methods of treating, inhibiting and preventing tumor growth and cancers such as, e.g. brain tumors (including meningiomas, glioblastoma multiforme, anaplastic astrocytomas, cerebellar astrocytomas, other high-grade or low-grade astrocytomas, brain stem gliomas, oligodendrogliomas, mixed gliomas, other gliomas, cerebral neuroblastomas, craniopharyngiomas, diencephalic gliomas, germinomas, medulloblastomas, ependymomas. choroid plexus tumors, pineal parenchymal tumors, gangliogliomas, neuroepithelial tumors, neuronal or mixed neuronal glial tumors), lung tumors (including small cell carcinomas, epidermoid carcinomas, adenocarcinomas, large cell carcinomas, carcinoid tumors, bronchial gland tumors, mesotheliomas, sarcomas or mixed tumors), prostate cancers (including adenocarcinomas, squamous cell carcinoma, transitional cell carcinoma, carcinoma of the prostatic utricle, or carcinosarcomas), breast cancers (including adenocarcinomas or carcinoid tumors), or gastric, intestinal, or colon cancers (including adenocarcinomas, invasive ductal carcinoma, infiltrating or invasive lobular carcinoma, medullary carcinoma, ductal carcinoma in situ, lobular carcinoma in situ, colloid carcinoma or Paget's disease of the nipple), skin cancer (including melanoma, squamous cell carcinoma, tumor progression of human skin keratinocytes, basal cell carcinoma, hemangiopericytoma and Karposi's sarcoma), lymphoma (including Hodgkin's disease and non-Hodgkin's lymphoma), sarcomas (including osteosarcoma, chondrosarcoma and fibrosarcoma) as well as for the treatment of nervous system disorders.

Administration of the peptides of the invention may be combined with other cancer therapies, antitumor agents and chemotherapeutic agents such as an aromatase inhibitor, an anti-estrogen, an anti-androgen, a gonadorelin agonist, a topoisomerase I inhibitor, a topoisomerase II inhibitor, a microtubule active agent, an alkylating agent, a retinoid, a carotenoid, a tocopherol, a cyclooxygenase inhibitor, an MMP inhibitor, a mTOR inhibitor, an antimetabolite, a platin compound, a methionine aminopeptidase inhibitor, a bisphosphonate, an antiproliferative antibody, a heparanase inhibitor, an inhibitor of Ras oncogenic isoforms, a telomerase inhibitor, a proteasome inhibitor, a compound used in the treatment of hematologic malignancies, a Flt-3 inhibitor, an Hsp90 inhibitor, a kinesin spindle protein inhibitor, a MEK inhibitor, an antitumor antibiotic, a nitrosourea, a compound targeting/decreasing protein or lipid kinase activity, a compound targeting/decreasing protein or lipid phosphatase activity, any further anti-angiogenic compound, and combinations thereof. Specific examples of antitumor agents include, but are not limited to, azacitidine, axathioprine, bevacizumab, bleomycin, capecitabine, carboplatin, chlorabucil, cisplatin, cyclophosphamide, cytarabine, daunorubicin, docetaxel, doxifluridine, doxorubicin, epirubicin, etoposide, fluorouracil, gemcitabine, herceptin, idarubicin, mechlorethamine, melphalan, mercaptopurine, methotrexate, mitoxantrone, oxaliplatin, paclitaxel, tafluposide, teniposide, tioguanine, retinoic acid, valrubicin, vinblastine, vincristine, vindesine, vinorelbine, receptor tyrosine kinase inhibitors, and combinations thereof. Additional examples of antitumor or chemotherapeutic agents are known in the art.

The invention provides for methods of treating macular degeneration including wet and dry macular degeneration comprising administering the peptide of the invention. Wet macular degeneration occurs when abnormal blood vessels grow behind the macula. These vessels are fragile and can leak fluid and blood, which result in scarring of the macula and raise the potential for rapid, severe damage. Bruch's membrane breaks down, usually near drusen deposits. This is where new blood vessel growth, or neovascularization, occurs. Central vision can become distorted or lost entirely in a short period of time, sometimes within days.

For the methods of treating macular degeneration, ocular administration of the peptides of the invention is contemplated. In addition, administration of the peptides may be combined with the other therapeutic agents such as other antiangiogenic drugs such as Bevacizumab (Avastin), Ranibizumab (Lucentis), Pegaptanib (Macugen), Aflibercept (Eylea), Lodamin (a polymeric formulation of TNP-470), Verteporfin (Visudyne) (Photodynamic Therapy or PDT), oligonulcoetide therapies, antibodies to Dr5, small molecule kinase modulators targeting c-Met, quinolone derivatives, fused bicyclic pyridine and pyrazine derivatives, or pyrrolopyrimidine compounds as inhibitors of CDK4/6. Additional therapeutic agents are known in the art. In addition, administration of the peptides of the invention for treating macular degeneration may be combined with other procedures such as an implantable telescope, laser photocoagulation and macular translocation surgery.

Provided herein is a method of treating a disorder associated with VEGF-induced vascular permeability. For example, the invention provides for methods of treating visual impairment or vision loss (blindness), macular degeneration, central retinal vein occlusion, branch retinal venin occlusion proliferative diabetic retinopathy, neovascular age-related macular degeneration (AMD), retinopathy of prematurity, ischemic retinopathy, intraocular neovascularization, corneal neovascularization, retinal neovascularization, choroidal neovascularization, diabetic macular edema, diabetic retina ischemia, diabetic retinal edema, and proliferative diabetic retinopathy, rubeosis iridis, neovascular glaucoma, retinoblastoma, uveitis and corneal graft neovascularization.

Subject

The subject may be a mammal, which may be a human. Prior to diagnosis, the subject may be at risk for cancer because of exposure to one or more risk factors or have a genetic risk for developing cancer. The one or more risk factors may include, for example, the subject having a family history of cancer, age, smoking tobacco, sun exposure, drinking alcoholic beverages, lack of physical activity, obesity and/or dietary deficiency.

Prior to diagnosis, the subject may be at risk of developing macular degeneration because exposure to one or more risk factors or have a genetic risk for developing macular degeneration. The one or more risk factors may include, for example, the subject having a family history of macular degeneration, age, smoking tobacco, prolonged sun exposure, high fat diet, dietary deficiency, high blood pressure, obesity, and/or light color eyes.

Administration

Suitable methods of administering a physiologically-acceptable composition, such as a pharmaceutical composition comprising a compound and/or micelle described herein, are well known in the art. Although more than one route can be used to administer a peptide, a particular route can provide a more immediate and more effective reaction than another route. Depending on the circumstances, a pharmaceutical composition comprising the peptide is applied or instilled into body cavities, absorbed through the skin or mucous membranes, ingested, inhaled, and/or introduced into circulation. For example, in certain circumstances, it will be desirable to deliver the pharmaceutical composition orally; through injection or infusion by intravenous, intratumoral, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means; by controlled, delayed, sustained or otherwise modified release systems; or by implantation devices. In one aspect, drug exposure can be optimized by maintaining constant drug plasma concentrations over time. Such a steady-state is generally accomplished in clinical settings by continuous drug infusion at doses depending on the drug clearance and the plasma concentration to be sustained. If desired, the composition is administered regionally via intratumoral, administration, intrathecal administration, intracerebral (intra-parenchymal) administration, intracerebroventricular administration, or intraarterial or intravenous administration targeting the region of interest. Alternatively, the peptide is administered locally via implantation of a matrix, membrane, sponge, or another appropriate material onto which the desired compound has been absorbed or encapsulated. Where an implantation device is used, the device is, in one aspect, implanted into any suitable tissue or organ, and delivery of the desired compound is, for example, via diffusion, timed-release bolus, or continuous administration.

Ocular administration of the peptides may be carried using intraocular implants, intravitreal injections, systemic administration, topical application, nanoparticles, microparticles, eye drops, bioadhesive gels or fibrin sealant, polysaccharides to modulate the permeability of the epithelial cell barrier complex, peptide enhances corneal drug delivery, mucosal administration such as administration using a biovector polymer, aqueous opthamalic sprays and electrodynamic ocular spray treatment. In one particular embodiment, the peptide may administered by intravitreal injection or topically such as in the form of an eye drop.

The peptide may be administered as a monotherapy or simultaneously or metronomically with other treatments, which may be a surgery or removal of a tumor. The term "simultaneous" or "simultaneously" as used herein, means that the peptide and other treatment be administered within 48 hours, preferably 24 hours, more preferably 12 hours, yet more preferably 6 hours, and most preferably 3 hours or less, of each other. The term "metronomically" as used herein means the administration of the peptide at times different from the other treatment and at a certain frequency relative to repeat administration. For example, the peptide of the invention may be administered with one or more VEGF inhibitors. For example, the peptide of the invention may be administered with one or more VEGF inhibitors or in combination with laser treatment for vision loss.

The peptide may be administered at any point prior to another treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins. The peptide may be administered at any point prior to a second treatment of the peptide including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

The peptide may be administered at any point after another treatment including about 1 min, 2 mins., 3 mins., 4 mins., 5 mins., 6 mins., 7 mins., 8 mins., 9 mins., 10 mins., 15 mins., 20 mins., 25 mins., 30 mins., 35 mins., 40 mins., 45 mins., 50 mins., 55 mins., 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, 48 hr, 50 hr, 52 hr, 54 hr, 56 hr, 58 hr, 60 hr, 62 hr, 64 hr, 66 hr, 68 hr, 70 hr, 72 hr, 74 hr, 76 hr, 78 hr, 80 hr, 82 hr, 84 hr, 86 hr, 88 hr, 90 hr, 92 hr, 94 hr, 96 hr, 98 hr, 100 hr, 102 hr, 104 hr, 106 hr, 108 hr, 110 hr, 112 hr, 114 hr, 116 hr, 118 hr, and 120 hr. The peptide may be administered at any point prior after a second treatment of the peptide including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

Formulation

The method may comprise administering the peptide. Peptides provided herein may be in the form of tablets or lozenges formulated in a conventional manner. For example, tablets and capsules for oral administration may contain conventional excipients may be binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers may be lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants may be potato starch and sodium starch glycollate. Wetting agents may be sodium lauryl sulfate. Tablets may be coated according to methods well known in the art.

Peptides provided herein may also be liquid formulations such as aqueous or oily suspensions, solutions, emulsions, syrups, and elixirs. The peptides may also be formulated as a dry product for constitution with water or other suitable vehicle before use. Such liquid preparations may contain additives such as suspending agents, emulsifying agents, nonaqueous vehicles and preservatives. Suspending agent may be sorbitol syrup, methyl cellulose, glucose/sugar syrup, gelatin, hydroxyethylcellulose, carboxymethyl cellulose, aluminum stearate gel, and hydrogenated edible fats. Emulsifying agents may be lecithin, sorbitan monooleate, and acacia. Nonaqueous vehicles may be edible oils, almond oil, fractionated coconut oil, oily esters, propylene glycol, and ethyl alcohol. Preservatives may be methyl or propyl p-hydroxybenzoate and sorbic acid. In particular, the peptides of the invention may be in aqueous formulations for topical administration such as in the form of an eye drop.

Peptides provided herein may also be formulated as suppositories, which may contain suppository bases such as cocoa butter or glycerides. Peptides provided herein may also be formulated for inhalation, which may be in a form such as a solution, suspension, or emulsion that may be administered as a dry powder or in the form of an aerosol using a propellant, such as dichlorodifluoromethane or trichlorofluoromethane. Peptides provided herein may also be formulated as transdermal formulations comprising aqueous or nonaqueous vehicles such as creams, ointments, lotions, pastes, medicated plaster, patch, or membrane. Peptides provided herein may also be formulated for parenteral administration such as by injection, intratumor injection or continuous infusion. Formulations for injection may be in the form of suspensions, solutions, or emulsions in oily or aqueous vehicles, and may contain formulation agents including, but not limited to, suspending, stabilizing, and dispersing agents. The peptide may also be provided in a powder form for reconstitution with a suitable vehicle including, but not limited to, sterile, pyrogen-free water.

Peptides provided herein may also be formulated as a depot preparation, which may be administered by implantation or by intramuscular injection. The peptides may be formulated with suitable polymeric or hydrophobic materials (as an emulsion in an acceptable oil, for example), ion exchange resins, or as sparingly soluble derivatives (as a sparingly soluble salt, for example).

Dosage

The method may comprise administering a therapeutically effective amount of the peptide to a patient in need thereof. The therapeutically effective amount required for use in therapy varies with the nature of the condition being treated, the length of time desired to activate TLR activity, and the age/condition of the patient. In general, however, doses employed for adult human treatment typically are in the range of 0.001 mg/kg to about 200 mg/kg per day. The dose may be about 0.05 mg/kg to about 10 g/kg per day. The desired dose may be conveniently administered in a single dose, or as multiple doses administered at appropriate intervals, for example as two, three, four or more sub-doses per day. Multiple doses may be desired, or required.

The dosage may be at any dosage such as about 0.05 µg/kg, 0.06 µg/kg, 0.07 µg/kg, 0.08 µg/kg, 0.09 µg/kg, 0.1 µg/kg, 0.2 µg/kg, 0.3 µg/kg, 0.4 µg/kg, 0.5 µg/kg, 0.6 µg/kg, 0.7 µg/kg, 0.8 µg/kg, 0.9 µg/kg, 1 µg/kg, 1.5 µg/kg, 2 µg/kg, 3 µg/kg, 4 µg/kg, 5 µg/kg, 10 µg/kg, 15 µg/kg, 20 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg.

The dosage may be at any dosage such as about 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 25 mg/kg, 50 mg/kg, 75 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 525 mg/kg, 550 mg/kg, 575 mg/kg, 600 mg/kg, 625 mg/kg, 650 mg/kg, 675 mg/kg, 700 mg/kg, 725 mg/kg, 750 mg/kg, 775 mg/kg, 800 mg/kg, 825 mg/kg, 850 mg/kg, 875 mg/kg, 900 mg/kg, 925 mg/kg, 950 mg/kg, 975 mg/kg, 1 g/kg, 2 g/kg, 3 g/kg, 4 g/kg, 5 g/kg, 6 g/kg, 7 g/kg, 8 g/kg, 9 g/kg, or 10 g/kg.

Kit

Provided herein is a kit, which may be used for treating a disorder associated with VEGF-induced vascular permeability or angiogenesis. The kit may comprise one or more of the peptides. The peptides may be part of a pharmaceutical composition. The kit may further comprise instructions for using the kit and conducting the administering the peptide or formulation.

The kit may also comprise one or more containers, such as vials or bottles, with each container containing a separate reagent. The kit may further comprise written instructions, which may describe how to perform or interpret the method described herein.

EXAMPLES

Example 1

Role of EB3 Interaction with IP3R in the Mechanism of IP3-Gated Release of Ca2+

It was determined whether allosteric modulation of EB3 function with the peptides of the invention (SEQ ID NO: 1 and SEQ ID NO: 3) inhibits both VEGF-induced vascular leakage and angiogenesis. Mice were challenged with VEGF or angiogenesis by subcutaneous injection of the matrigel, tumor cells or laser burn of Bruch's membrane.

Figure 3:
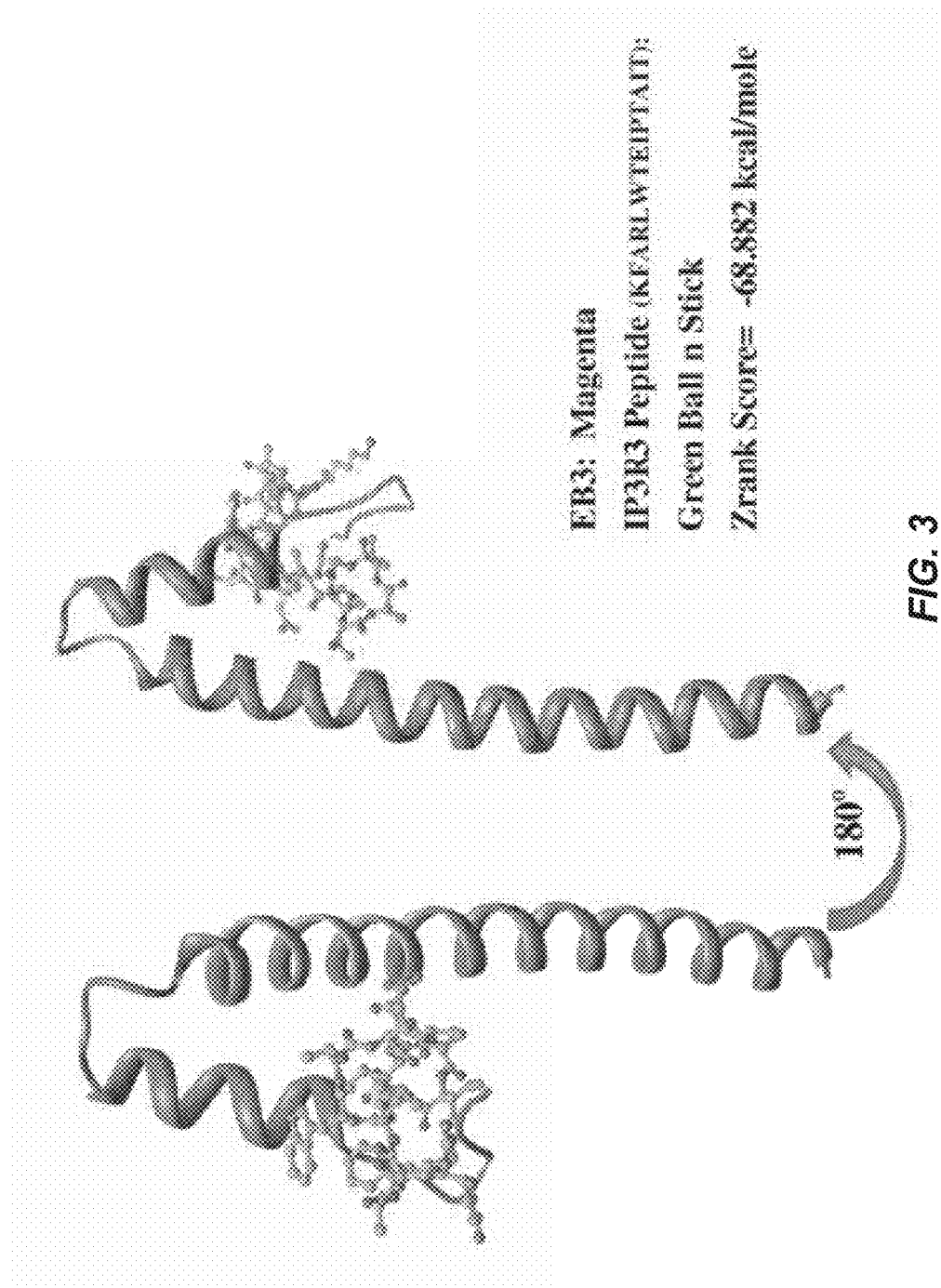
FIG. 3 shows a ribbon representation of EB3 structure (magenta) and $IP_3R_3$ derived peptide (SEQ ID NO: 1) docked into EB3 hydrophobic binding groove of EB3; 180° rotation is shown. The $IP_3R_3$ derivative peptide was docked using a Z-Dock program in conjunction with Discovery Studio 3.0 software. The binding energy between the peptide and EB3 was calculated to be −68.882 kcal/mol.
Figure 4A:
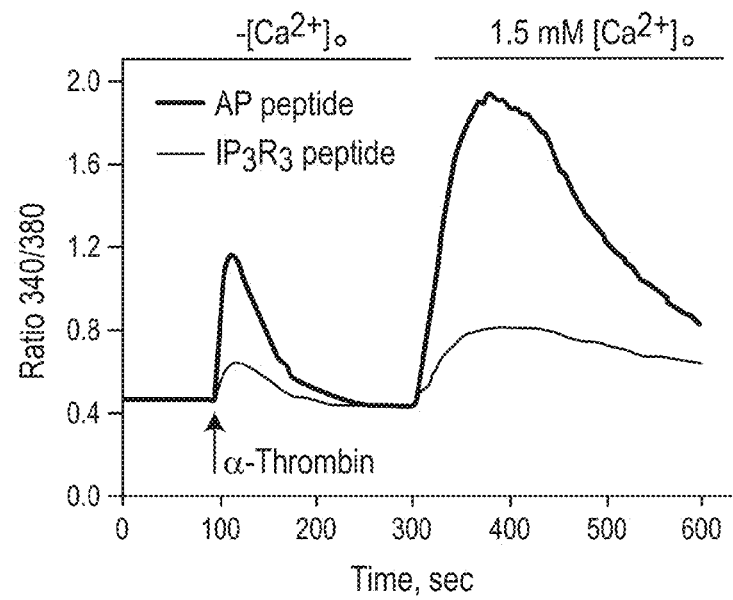
FIG. 4A-4B shows $IP_3R_3$ peptide (SEQ ID NO: 1) inhibits $Ca^{2+}$ release from ER in response to PAR-1 activation.
Figure 4B:
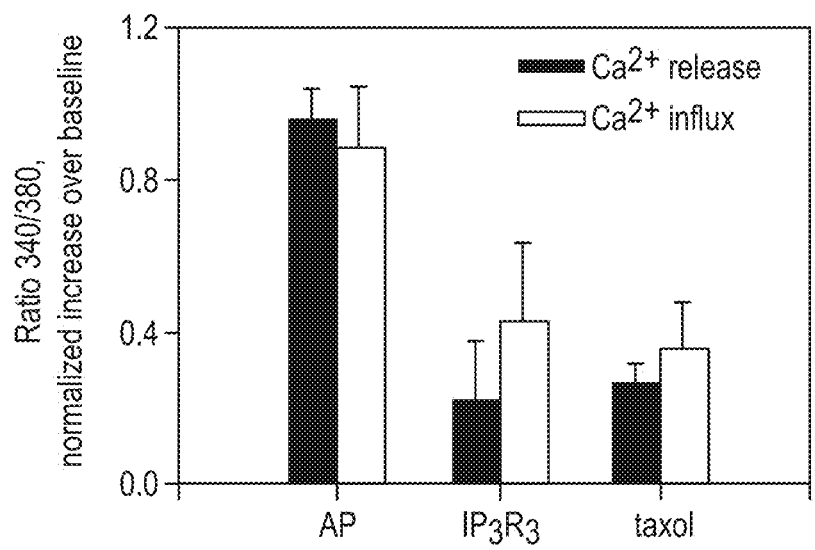

$IP_3R_5$ contains EB binding consensus motif, Ser/Thr-x-Ile-Pro (SxIP) (SEQ ID NO: 5). A short peptide based on IP.sub.3R.sub.3 sequence (KFARLWTEIPTAIT—SEQ ID NO: 1) (FIG. 2) shows high binding activity for EB3 with free energy binding of −68.882 kcal/mol (FIG. 3). The role of the interaction between EB3 and $IP_3R_3$ was recently described by Geyer et al., Cell Rep 12(1):79-89; 2015. The pre-treatment of cell with $IP_3R_3$ sequence attached to the C-terminus of cell permeant antennapedia peptide (AP) at 10 nM markedly decreased the release of Ca2+ from stores in response to thrombin (FIG. 4A), suggesting that interaction between IP.sub.3R.sub.3 and EB3 is critical in the mechanism of $IP_3R_3$ activation. The effects of $IP_3R_3$ peptide and taxol were compared in regulating $Ca^{2+}$ release. It was found that pre-treatment of cells with 5 µg/ml taxol for 20 min prior to thrombin stimulation inhibits release of $Ca^{2+}$ from ER to the same extent as $IP_3R_3$ peptide (FIG. 4B).

Example 2

Structure-Based Design of End Binding Inhibitory Peptide (EBIN)

End Binding Inhibitory peptide, namely EBIN, was designed based on computational in silico alanine-scanning and fully-flexible docking of IPR peptide to the EB binding pocket (Tables 2 and 3). Binding free energy (ΔG) was used to determine a contribution of each residue in stabilization of interaction of the peptide with EB protein.

The following criteria were used: ΔG value≥1=Stabilizing residue ΔG value≥−1=Destabilizing residue ΔG value<−1 to 0 to <1=Neutral residue Alanine scanning reveals stabilizing (with a positive binding energy of 0.50 Kj/mole or more; shown in black) and destabilizing (with a negative binding energy of −1, shown in blue) residues.

TABLE 1

Computed changes in binding free energy after truncation of amino acid residues which surround Thr-x-Pro motif of $IP_3R_3$

| Peptide Sequence | Free Energy Binding (-kcal/mole) | SEQ ID NO |
|---|---|---|
| KFARLWTEIPTAIT ($IP_3R_3$ peptide) | −68.882 | 1 |
| FARLWTEIPTAIT | −68.809 | 6 |
| RLWTEIPTAIT | −46.571 | 7 |
| LWTEIPTAIT | −54.443 | 8 |
| WTEIPTAIT | −42.886 | 9 |
| TEIPTAIT | −37.16 | 10 |
| TEIPTAI | −39.337 | 11 |
| TEIPTA | −41.234 | 12 |
| TEIPT | −34.5 | 13 |
| FARLWTEIPTAI | −51.42 | 14 |
| TEIP | −45.071 | 15 |
| RTEIPTI | −49.74 | 16 |
| FRTEIPTI | −40.728 | 17 |
| FTKIPTI | −55.469 | 18 |
| KFARTKIPTAIT | −57.32 | 19 |
| FARTEIPTAI | −33.415 | 20 |
| KFARTEIPTAIT | −55.736 | 21 |

TABLE 2

Computed Changes in binding free energy after mutating each amino acid residue of $IP_3R_3$ for alanine: $K_1F_2A_3R_4L_5W_6T_7E_8I_9P_{10}T_{11}A_{12}I_{13}T_{14}$

| Amino acid | ΔG |
|---|---|
| K1 | 0.25 |
| F2 | 0.52 |
| R4 | 0.01 |
| L5 | −1.03 |
| W6 | −1.08 |
| T11 | 0.91 |
| I13 | 1.33 |
| T14 | 0.40 |

TABLE 3

Computed Changes in binding free energy after mutating each amino acid residue of EBIN for alanine.

| Amino acid | ΔG |
|---|---|
| F1 | 1.64 |
| T2 | 1.07 |
| E3 | 0.02 |
| I4 | 0.68 |
| T11 | 0.98 |
| I7 | 0.94 |

Figure 5:
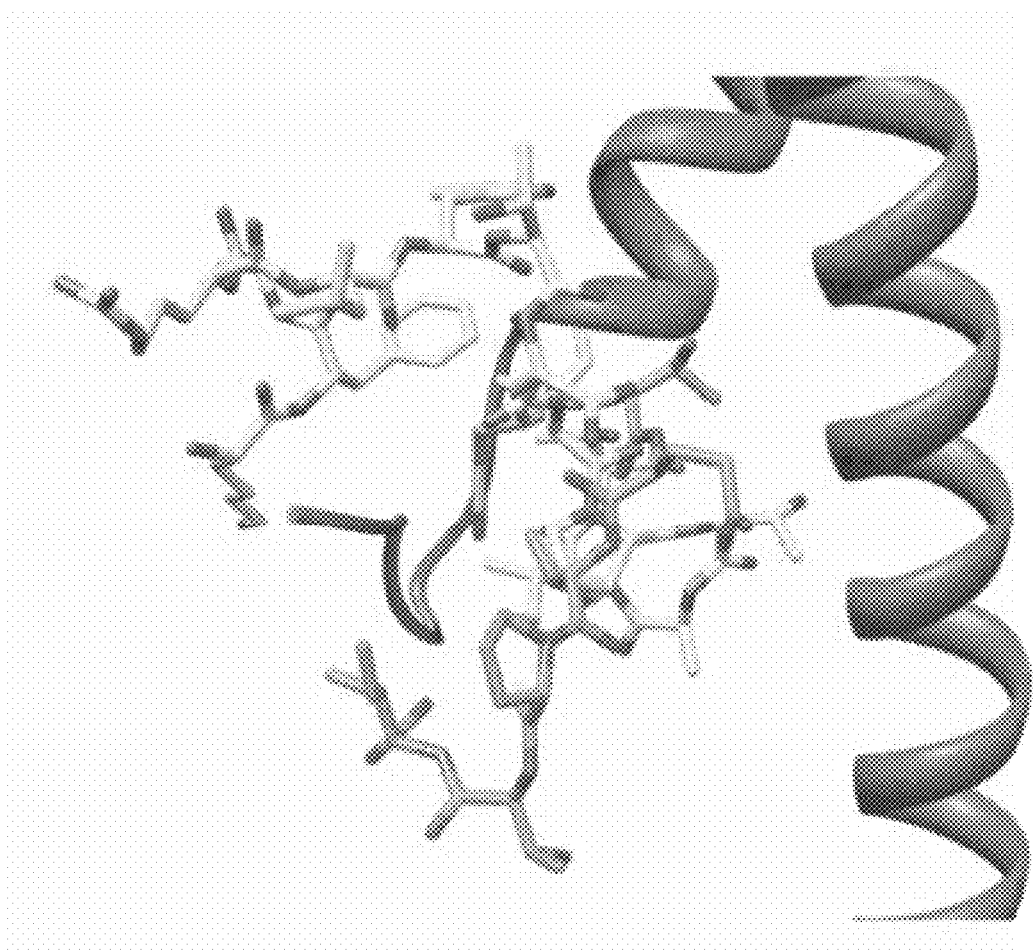
FIG. 5 shows a ribbon representation of EB3 in the complex with EBIN (SEQ ID NO: 3) and $IP_3R_3$ peptide (SEQ ID NO: 1). The computed binding energy is −68.882 and −60.251 for IPR and EBIN, respectively.

As a result, the 14 amino acid IPR peptide was reduced to the 7 amino acid End Binding Inhibitory peptide (EBIN; FTEIPTI (SEQ ID NO: 3). FIG. 5 demonstrates the interaction between EB3 and EBIN. Similarly to $IP_3R_3$ (is shown in yellow stick in FIG. 5), EBIN binds to hydrophobic grove between EB acidic tail and coil-coiled domain. The calculated energy binding of EBIN to EB3 is −60.251 kcal/mol, which is similar to the energy binding between IPR and EB3. Threonine at position 2 of EBIN plays a critical role in binding to the EB3 interface because mutation of this residue to alanine completely abolishes the binding. Therefore, a single amino-acid mutation T→A peptide, FAEIPTI (SEQ ID NO: 4), was used as a loss-of-binding control.

Example 6

EBIN Prevented VEGF-Induced Microvascular Leakage

VE-cadherin is the main adhesion protein of inter-endothelial junctions that bridges endothelial cell into continuous monolayer in order to maintain restrictive barrier of the vessel wall to protein rich fluids. Both VEGF and Ang2 destabilizes VE-cadherin adhesion either directly, by inducing tyrosine phosphorylation of VE-cadherin and targeting VE-cadherin for internalization and degradation, or indirectly, by mean of disruption of VE-cadherin adhesion due to response to intracellular forces.

A critical cross-interaction between VE-cadherin adhesion and microtubule cytoskeleton was recently described (Komarova et al. *Molecular Cell* 48(6): 914-25; 2012.). Calcineurin, a calcium-dependent phosphatase, was found to be the main signaling player in this cross-interaction as it de-phosphorylates EB3, promotes EB3-dependent re-organization of MT cytoskeleton and thus provides a forward-feed mechanism for disruption of VE-cadherin adhesion.

Figure 6B:
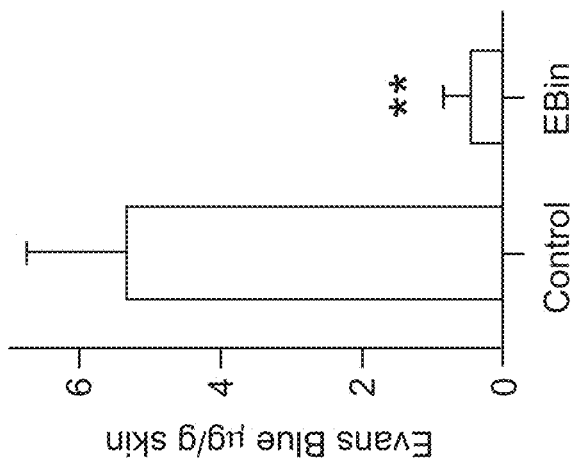
FIG. 6A-6B.
Figure 6A:
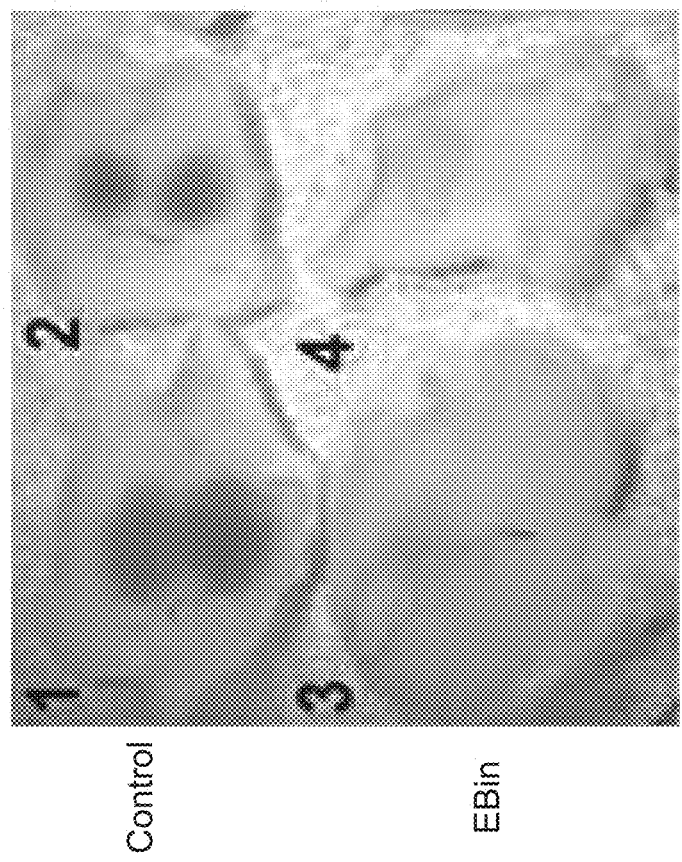

A study investigating whether injection of the EBIN prevented vascular endothelial growth factor (VEGF)-induced microvascular leakage was carried out. Balb/cJ mice were pretreated with the EBIN peptide (1 μM/kg) or a control peptide (2T→A mutation) and then human VEGF (50 ng/kg body weights) was intradermally injected to induce vascular leakage of albumin-bound Evans Blue (see FIG. 6A). In addition, the formamide-extracted Evans Blue was quantified spectrophotometically at 620 nm and corrected for hemoglobin (740 nm) and skin weight (see FIG. 6B). The data provided in FIG. 6 demonstrated that treatment of animals with the EBIN peptide significantly inhibited subcutaneous vascular leak as induced by intradermal injection of human VEGF and thus fully supports that EBIN may represent a novel potent therapy for inhibiting angiogenesis and for the treatment of disorders associated with VEGF-induced vascular permeability.

Example 7

EBIN Abolished Blood Vessel Growth in Models of Angiogenesis

The effect of EBIN on in vitro tubulogenesis and in vivo angiogenesis was investigated using matrigel models. A single cell suspension of human umbilical vein endothelial cells was plated above matrigel-coated wells in the presence of 1 µM EBIN or control peptide; tube formation was assessed 16 hours later. As shown in FIGS. 7A and 7B, EBIN significantly abolished formation of tubes in this in vitro 2D matrigel model.

EBIN effect on blood vessels ingrowth in an in vivo model of ectopic matrige angiogenesis was also investigated. Blood vessel in growth matrigel was pre-mixed with heparin and VEGF but not with endothelial cells, and i.p. injected into low abdomen of mice. There were two 400 µL plugs per mouse. In the mice treated with the control peptide (Group 1), newly formed blood vessels grew into the matrigel (FIG. 7C, 1). These vessels were functional and perfused with blood that is apparent from the presence of red blood cells inside the vessels. In addition, mice were treated with EBIN at the time of matrigel injection (FIG. 7C, 2; Group 2) or 36 hrs after matrigel (FIG. 7C, 3; Group 3). Matrigel plugs were removed at 96 hours, fixed and stained with HE to assess the vessel formation. The number of vessels was markedly reduced indicating for the significant reduction in the blood vessels ingrowth with 99% confidence. It should be noted that post-treatment was as effective as a treatment suggesting that similar to anti-VEGF therapy and taxol, EBIN can cause vessel regression. Although, EBIN did not induce endothelial cell death or cell cycle arrest (data not shown).

Example 8

EBIN Inhibited Tumor Cell Growth

The effect of EBIN on growth rate of triple negative (estrogen receptor [ER], progesterone receptor [PR] and human epidermal growth factor receptor-2 [HER-2] are not expressed in this cell line) human breast cancer cells using a xenograft model was investigated. Nude mice (n=8 mice per group) were injected with $3 \times 10^6$ MDA-MB-231 human breast cancer cells into the upper left mammary fat pad. All mice developed the tumor by day 13. At that time point, mice were randomized and divided by 5 groups and each group received the treatment. Study was terminated at day 24 when the tumor reached 2000 mm$^3$ in size. The treatment with control peptide and EBIN was performed daily for 7 days. EBIN and control peptide were delivered via tail vein injection. Control peptide was injected at 5 µM/kg body weight. EBIN was injected at 1 µM/kg and 5 µM/kg body weight.

Figure 8B:
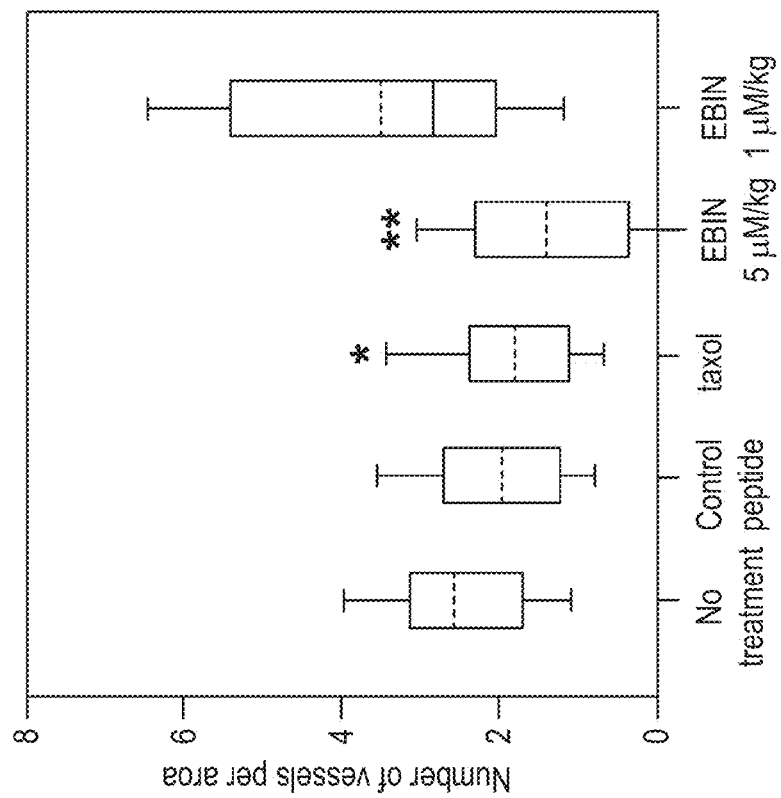
FIG. 8A-8B shows the effect of EBIN treatment on the tumor growth curve and neovascularization.
Figure 8A:
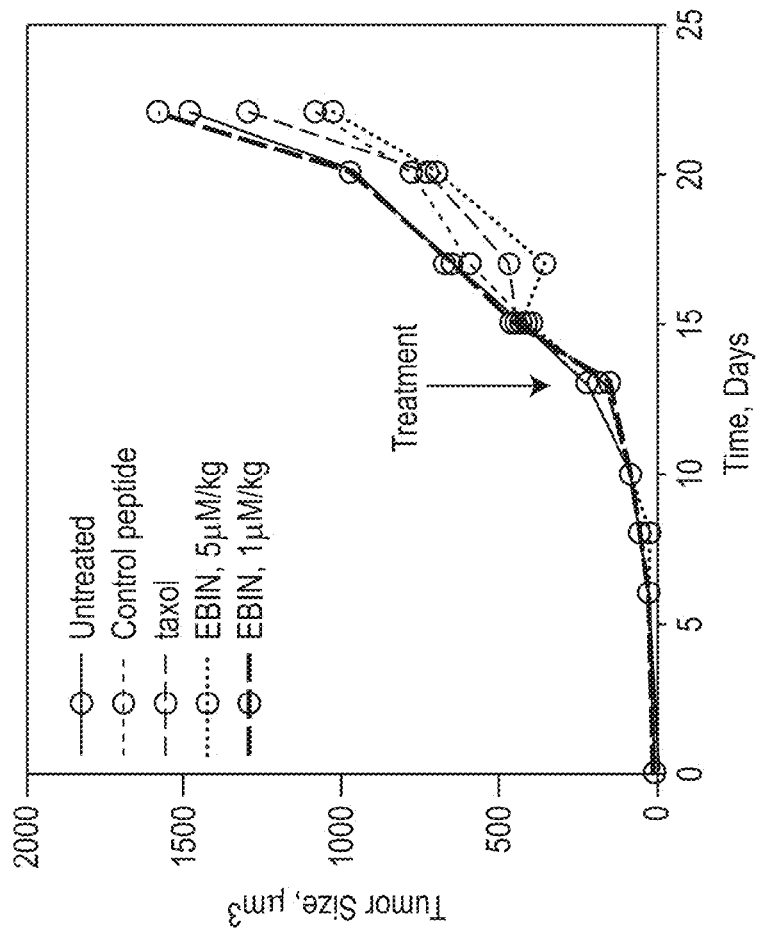

Treatment with taxol was performed via intraperitoneal injection at 10 µM/kg body weight for 4 days. Tumor size was measured 3 times a week. As shown in FIG. 8A, a significant delay in the tumor growth in taxol group was observed and reduction in the tumor size in EBIN-treated group was observed after 4 treatments. This effect was rather transient, although, the size of tumors in EBIN-treated group was significantly smaller as compared to control untreated group. Mice treated with 1 µM/kg EBIN developed the tumor at the same rate as untreated mice suggesting that the low dose was not affective.

To correlate the effect of EBIN treatment with tumor neovascularization, tumor tissue was collected, fixed and stained with hematoxylin and eosin (H&E). Number of cells outside of the tumor mass was scored and normalized per area. Consistent with the tumor growth curve, the number of vessels outside of the tumor was significantly reduced only in taxol and EBIN (5 µM/kg)-treated groups. EBIN showed superior effect as compared to taxol (see FIG. 8B). All other groups showed no difference as compared to untreated group. These data suggest that EBIN demonstrates anti-angiogenic properties and can be used to treatment of pathological angiogenesis. Only treatment with taxol and EBIN at dose 5 µM/kg body weight significantly reduced the number of vessel outside of the tumor.

Example 9

Determining the Efficacy of EBIN to Treat In Vivo Models of Laser-induced Choroidal Neovascularization (CNV)

Neovascular AMD is characterized by growth of the blood vessels from the choroid, which penetrate through Bruch's membrane into the subretinal area. The mouse model of laser-induced Choroidal neovascularization (CNV) is a well-established model of the exudative form of AMD. The disruption of Bruch's membrane by a laser beam promotes the growth of new choroidal vessels into the retina thus mimicking the pathological conditions of AMD (FIG. 9). This model has been successfully used in predicting the clinical efficacy of VEGF therapy for neovascular AMD.

To assess the barrier-protective and anti-angiogenic activities of EBIN, EBIN is tested in murine models of CNV. In addition to treatment with EBIN, LEAF™ antibody (a monoclonal rat antibody against mouse VEGF-A) and control peptide (Myr-FAEIPTI), were used as positive and negative experimental controls, respectfully.

Figure 10:
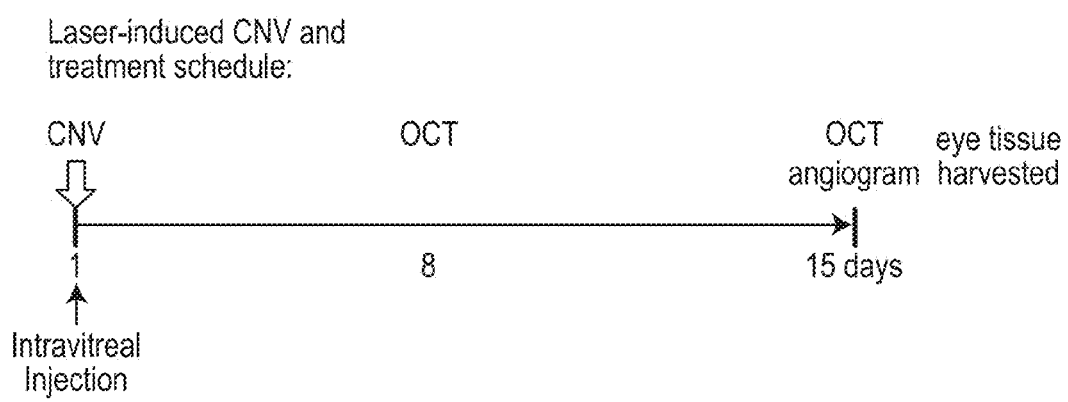
FIG. 10 shows an outline of the schedule for the Laser-induced CNV, Ocular Coherence Tomography (OCT), Fundus Fluorescein Angiography, treatment and tissue harvest for groups 1-3 (as set out in Table 4).

C57/BL6 mice (6-8 week old) were purchased from Charles River Laboratory and used according to an approved protocol. Mice were anesthetized with a mixture of ketamine/xylazine (100 mg/5 mg/kg IP) and their pupils were dilated with a topical application of Cyclomydril (Alcon Laboratories, Fort Worth, Tex.). The fundus was viewed with an imaging camera, and laser photocoagulation was induced using the image-guided laser system (Micron IV, Phoenix Research Laboratories, Pleasanton, Calif.). Four laser burns at equal distance from the optic nerve were induced one by one in right eye by a green Argon laser pulse with a wavelength of 532 nm, a fixed diameter of 50 µm, duration of 70 ms, and power levels from 210-250 mW. Appearance of bubble or a small subretinal hemorrhage (diameter <1 mm) at the laser spot serves to indicate rupture of the Bruch's membrane and as confirmation of laser-induced CNV. This procedure was performed only on the right eye of each mouse. The schedule of laser-induced photocoagulation and treatment protocol is shown in FIG. 10. Treatment with control and EBIN peptides (1 µg/eye) and an antibody against mouse VEGF-A (2 µg/eye; LEAF™; Low Endotoxin, Azide-Free) were administrated once to the right eye via intravitreal injection (2 µl) after the laser photocoagulation. The eyes were gently rinsed with sterile saline to remove the lubricating eye drops and treated with an antibiotic ointment, erythromycin (Fougera, Melville, N.Y.). Mice were then placed on a pre-warmed warming plate at 35° C. after the laser treatment until they awakened. The EBIN anti-angiogenic efficacy was evaluated by ocular coherence tomography (OCT) at days 8 and 15, angiogram was performed on day 15 only (FIG. 10). Fluorescein angiography and OCT are performed for imaging the retinal vasculature, similar to the procedure routinely used clinically for patients. This is performed via intravenous injection of 10 μl of 0.2% fluorescent dye through a tail vein of the mice. A sample size of 10 mice per treatment group provides sufficient power to detect a hypothesized 10% difference in vascular leakage (lesson area) based on the parameters determined in Gong et al., *PLoS One* 2015, 10(7): e 0132643.

Table 4 lists the ten treatment groups (n=10 CNV mice per treatment group, 30 mice in total), drug regimen and intended endpoints for measuring the response to treatment. Group 1 mice received Myr-control peptide, group 2 mice were treated with Myr-EBIN and group 3 mice were treated with the LEAF™ antibody as a positive control. All treatments are delivered as a single injection at time of CNV via intravitreal route as outlined in FIG. 10.

TABLE 4

Treatment groups, drug regimen and endpoint assays for measuring the response to treatment of CNV in mice.

| Group | N | Drug | Regimen | Endpoint assays |
|---|---|---|---|---|
| 1 | 10 | Myr-control peptide (1 μg/eye) | Intravitreal injection of 1 μg/eye in 1 ul; on day 1 (at the time of CNV) | 1. Fluorescein angiography on day 15 and OCT at days 8 and 15 |
| 2 | 10 | Myr-EBIN intravitreal (1 μg/eye) | Intravitreal injection of 1 μg/eye in 1 ul; on day 1 (at the time of CNV) | 2. Eye collection for histopathologic examination on day 15 |
| 3 | 10 | LEAF ™ antibody | Intravitreal injection of 2 μg/eye in 1 ul (equivalent to 2.5 mg dose in human); on day 1 (at the time of CNV) | |
| Total | 30 | | | |

FIGS. 11a and 11b show images of Fundus Fluorescein Angiography (a) and corresponding Optical Coherence Tomography (b) at day 15 post laser photocoagulation (numbers indicate corresponding CNV lesions) for EBIN, anti-VEGF antibody or control peptide treated CNV mice. EBIN reduced the CNV lesions similar to anti-VEGF treatment and hence, provides potent alternative to current treatment of eye disease such as macular degeneration. The experiments were terminated at day 15, at which time, the animals were sacrificed with ketamine/xylazine (100 mg/5 mg/kg IP) followed by cervical dislocation and eye tissue was collected for immunofluorescent staining and pathological analysis. The flat mount preparations of retina/choroid/sclera were used for staining with Alexa594-labled lectin from *Bandeiraea simplicifolia* (B4) for post-mortem analysis of CNV area (FIG. 11c).

Data analyses were performed using exclusion criteria established in previous studies (Gong et al., *PLoS One* 2015, 10(7): e 0132643). Cases of severe hemorrhages, such as excessive laser burns that damage not only Bruch's membrane but also the choroid and retinal pigment epithelium, fused lesions, the lesion that more than 5 times larger than the mean of the lesions under the same experimental conditions, were excluded. The area of vascular leakage and CNV were quantified using fluorescein angiography images and confocal images of CNV staining for lectin B4 using MetaMorph software. Data were plotted using Sigma Plot software (FIG. 11d and 11e) and analyzed by one-way ANOVA using Prism 6 (GraphPad, SanDiego, Calif.).

Further Studies

The treatment of mice with EBIN significantly reduced both the vascular leakage and CNV lesions compared with control peptide treated mice (FIG. 11). The effect of EBIN was similar to LEAF™ treatment suggesting that EBIN might provide a cost effective and efficient alternative to currently available anti-VEGF treatment of AMD such as bevacizumab and aflibercept.

Alternatively, EBIN is delivered via an eye drop route. In this case, the treatment starts at one day prior the laser photocoagulation and mice are treated twice daily until 15 days post-laser photocoagulation. The duration of treatment and observation is 15 days. In addition, EBIN is delivered in combination with LEAF™ antibody via intravitreal injection and/or via an eye drop route. In all cases the LEAF™ antibody is administered via intravitreal injection. As described previously, the EBIN anti-angiogenic efficacy is evaluated by fluorescein angiography and ocular coherence tomography (OCT) at 8 and 15 days post laser-induced CNV. In addition, eye tissue is harvested on day 15.

Table 5 lists the ten treatment groups (n=10 CNV mice per treatment group, 100 mice in total), drug regimen and intended endpoint assays for measuring the response to treatment for future studies. Group 1 mice are treated with the LEAF™ antibody as a positive control and group 2 mice receive LEAF™ Purified Rat IgG2a, κ Isotype Ctrl, as a control for group 1. Groups 3 and 4 are treated with a Decoy receptor for mouse VEGF (positive control 2) or negative Myr-control peptide, respectively. All LEAF™ antibodies, the Decoy receptor and control peptide are delivered as a single injection at time of CNV via intravitreal route. Groups 5 and 6 receive Myr-EBIN via intravitreal route, 0.1 μg/eye or 1 μg/eye, respectively. Groups 7 and 8 receive Myr-EBIN via eye drops, 0.5 μg/eye or 5 μg/eye, twice daily, respectively. Group 9 mice are treated with Myr-EBIN (0.1 μg/eye) in combination with LEAF™ antibody, both delivered via intravitreal route. Group 10 are treated with Myr-EBIN eye drops (0.5 μg/eye) in combination with LEAF™ antibody via intravitreal route.

TABLE 5

Future treatment groups, drug regimen and endpoint assays
for measuring the response to treatment of CNV in mice.

| Group | N | Drug | Regimen | Endpoint assays |
|---|---|---|---|---|
| 1 | 10 | LEAF ™ antibody | Intravitreal injection of 2 µg/eye in 1 ul (equivalent to 2.5 mg dose in human); on day 1 (at the time of CNV) | 1. Fluorescein angiography on day 15 and OCT at days 8 and 15 |
| 2 | 10 | LEAF ™ Purified Rat IgG2a, κ Isotype Ctrl | Intravitreal injection of 2 µg/eye in 1 ul (equivalent to 2.5 mg dose in human); on day 1 (at the time of CNV) | 2. Eye collection for histopathologic examination on day 15 |
| 3 | 10 | Decoy receptor for mouse VEGF | Intravitreal injection of 2 µg/eye in 1 ul on day 1 (at the time of CNV) | |
| 4 | 10 | Myr-control peptide (1 µg/eye) | Intravitreal injection of 1 µg/eye in 1 ul; on day 1 (at the time of CNV) | |
| 5 | 10 | Myr-EBIN intravitreal (0.1 µg/eye) | Intravitreal injection of 0.1 µg/eye in 1 ul; on day 1 (at the time of CNV) | |
| 6 | 10 | Myr-EBIN intravitreal (1 µg/eye) | Intravitreal injection of 1 µg/eye in 1 ul; on day 1 (at the time of CNV) | |
| 7 | 10 | Myr-EBIN eye drops (0.5 µg/eye) | Eye drops, 0.5 µg/eye; twice daily | |
| 8 | 10 | Myr-EBIN eye drops (5 µg/eye) | Eye drops, 5 µg/eye; twice daily | |
| 9 | 10 | Myr-EBIN intravitreal (0.1 µg/eye) + LEAF ™ antibody intravitreal | Group #1 in combination with group #5 | |
| 10 | 10 | Myr-EBIN eye drops (0.5 µg/eye) + LEAF ™ antibody intravitreal | Group #1 in combination with group #7 | |
| Total | 100 | | | |

Example 10

Acute Toxicity Testing of EBIN In Vivo

Figure 12A:
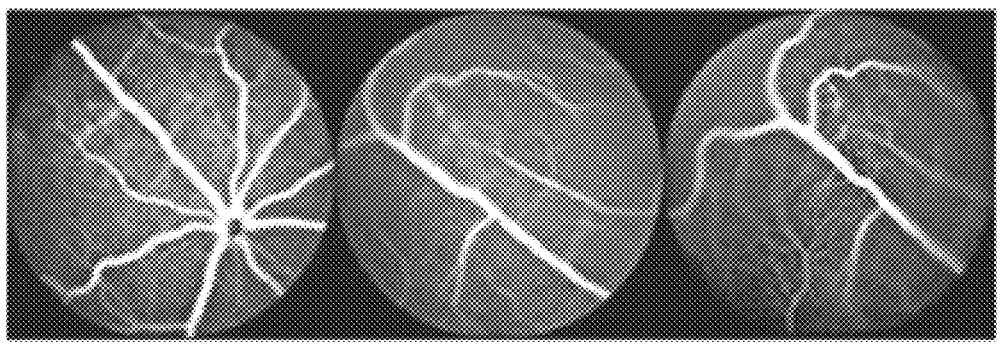
FIG. 12A-12B.
Figure 12B:
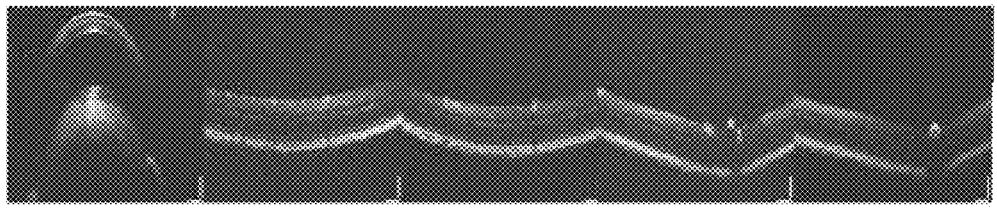

A short term study is designed to assess safety of administration in vivo. C57BL/6 mice (n=10, 5 mice per group/treatment route) are randomized and divided into two groups. The first group is treated with EBIN in the right eye via eye drops delivered twice daily, 5 µg per eye (10 µl) and, the second group is treated with intravitreal injection of EBIN in the right eye at the maximum dose, 1 µg per eye (2 µl) on day one. The intravitreal injection is performed under ketamine/xylazine (100 mg/5 mg/kg) anesthesia. Both groups are monitored daily for general health including body weight as well as any eye abnormalities including opacity, exophthalmia enophthalmia, conjunctivitis, abnormal secretions or crusting, and corneal ulcers for a period of 8 days. Animals are subsequently subjected to fluorescein angiography and OCT imaging. No toxicity was observed following treatment with EBIN, either with or without CNV induction (FIG. 12).

What is claimed:

1. A method of inhibiting angiogenesis comprising administering to a patient in need thereof an isolated peptide comprising the amino acid sequence of KFARLWTEIPTAIT (SEQ ID NO: 1) or FTEIPTI (SEQ ID NO: 3), wherein the patient is suffering from cancer, visual impairment, vision loss (blindness), macular degeneration, central retinal vein occlusion, branch retinal vein occlusion proliferative diabetic retinopathy, neovascular age-related macular degeneration (AMD), retinopathy of prematurity, ischemic retinopathy, intraocular neovascularization, corneal neovascularization, retinal neovascularization, choroidal neovascularization, diabetic macular edema, diabetic retina ischemia, diabetic retinal edema, and proliferative diabetic retinopathy, rubeosis iridis, neovascular glaucoma, retinoblastoma, uveitis or corneal graft neovascularization.

2. The method of claim 1, wherein the isolated peptide is administered by intravitreal injection or topically.

3. The method of claim 1, wherein the peptide is linked to a carrier peptide.

4. The method of claim 3, wherein the carrier peptide is antennapedia peptide (AP), penetratin peptide, TAT, tranportan or polyarginine.

5. The method of claim 1, wherein the peptide is conjugated to a fatty acid.

6. The method of claim 5, wherein the peptide is myrisoylated.

7. The method of claim 1, wherein the isolated peptide is administered in combination with one or more VEGF inhibitors.

8. The method of claim 1, wherein the isolated peptide is administered in combination with laser treatment of eye disease.

9. The method of claim 1, wherein the isolated peptide is administered in combination with a steroid.

10. A method of treating a disorder associated with VEGF-induced vascular permeability comprising administering to a patient in need thereof an isolated peptide comprising the amino acid sequence of KFARLWTEIPTAIT (SEQ ID NO: 1) or FTEIPTI (SEQ ID NO: 3), wherein the disorder is cancer, visual impairment, vision loss (blindness), macular degeneration, central retinal vein occlusion, branch retinal vein occlusion proliferative diabetic retinopathy, neovascular age-related macular degeneration (AMD), retinopathy of prematurity, ischemic retinopathy, intraocular neovascularization, corneal neovascularization, retinal neovascularization, choroidal neovascularization, diabetic macular edema, diabetic retina ischemia, diabetic retinal edema, and proliferative diabetic retinopathy, rubeosis iridis, neovascular glaucoma, retinoblastoma, uveitis or corneal graft neovascularization.

11. The method of claim 10, wherein the isolated peptide is administered by intravitreal injection or topically.

12. The method of claim 10, wherein the peptide is linked to a carrier peptide.

13. The method of claim 12, wherein the carrier peptide is antennapedia peptide (AP), antennapedia peptide, penetratin peptide, TAT, tranportan or polyarginine.

14. The method of claim 10, wherein the peptide is conjugated to a fatty acid.

15. The method of claim 14, wherein the peptide is myrisoylated.

16. The method of claim 10, wherein the isolated peptide is administered in combination with one or more VEGF inhibitors.

17. The method of claim 10, wherein the isolated peptide is administered in combination with laser treatment of eye disease.

18. The method of claim 10, wherein the isolated peptide is administered in combination with a steroid.

* * * * *

UNITED STATES PATENT AND TRADEMARK OFFICE
CERTIFICATE OF CORRECTION

Page 1 of 1

PATENT NO. : 9,675,660 B2
APPLICATION NO. : 15/058938
DATED : June 13, 2017
INVENTOR(S) : Yulia A. Komarova et al.

It is certified that error appears in the above-identified patent and that said Letters Patent is hereby corrected as shown below:

In the Specification

At Column 1, Line 7, (approx.) immediately after the title, please insert the following title and accompanying paragraph:
--STATEMENT OF GOVERNMENTAL INTEREST
This invention was made with government support under grant nos. R01 HL045638 and R01 HL103922 awarded by the National Institutes of Health. The government has certain rights in this invention.--

Signed and Sealed this
Thirtieth Day of April, 2019

Andrei Iancu
*Director of the United States Patent and Trademark Office*

```
                      SEQUENCE LISTING

<160> NUMBER OF SEQ ID NOS: 21

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide

<400> SEQUENCE: 1

Lys Phe Ala Arg Leu Trp Thr Glu Ile Pro Thr Ala Ile Thr
 1               5                  10

<210> SEQ ID NO 2
<211> LENGTH: 14
<212> TYPE: PRT
<213> ORGANISM: Artificial Sequence
```

```
<220> FEATURE:
<223> OTHER INFORMATION: Synthetic peptide

<400> SEQUENCE: 2

Lys Phe Ala Arg Leu Trp Ala Glu Ile Pro Thr Ala Ile Thr
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Phe Thr Glu Ile Pro Thr Ile
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Phe Ala Glu Ile Pro Thr Ile
1               5

<210> SEQ ID NO 5
<211> LENGTH: 4
<212> TYPE: PRT
<213> ORGANISM: Artificial Sequence
<220> FEATURE:
<223> OTHER INFORMATION: Consensus motif sequence
<220> FEATURE:
<221> NAME/KEY: MISC_FEATURE
<222> LOCATION: (1)..(1)
<223> OTHER INFORMATION: Xaa is Ser or Thr
<220> FEATURE:
<221> NAME/KEY: MISC_FEATURE
<222> LOCATION: (2)..(2)
<223> OTHER INFORMATION: Xaa is any amino acid

<400> SEQUENCE: 5

Xaa Xaa Ile Pro
1

<210> SEQ ID NO 6
<211> LENGTH: 13
<212> TYPE: PRT
<213> ORGANISM: Artificial Sequence
<220> FEATURE:
<223> OTHER INFORMATION: Synthetic peptide

<400> SEQUENCE: 6

Phe Ala Arg Leu Trp Thr Glu Ile Pro Thr Ala Ile Thr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

<400> SEQUENCE: 7

Arg Leu Trp Thr Glu Ile Pro Thr Ala Ile Thr
```

```
1               5                   10
```

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

```
Leu Trp Thr Glu Ile Pro Thr Ala Ile Thr
1               5                   10
```

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

```
Trp Thr Glu Ile Pro Thr Ala Ile Thr
1               5
```

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

```
Thr Glu Ile Pro Thr Ala Ile Thr
1               5
```

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

```
Thr Glu Ile Pro Thr Ala Ile
1               5
```

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

```
Thr Glu Ile Pro Thr Ala
1               5
```

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

```
Thr Glu Ile Pro Thr
1               5
```

```
<210> SEQ ID NO 14
<211> LENGTH: 12
<212> TYPE: PRT
<213> ORGANISM: Artificial Sequence
<220> FEATURE:
<223> OTHER INFORMATION: Synthetic peptide

<400> SEQUENCE: 14

Phe Ala Arg Leu Trp Thr Glu Ile Pro Thr Ala Ile
1               5                   10

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide

<400> SEQUENCE: 15

Thr Glu Ile Pro
1

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Arg Thr Glu Ile Pro Thr Ile
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

Phe Arg Thr Glu Ile Pro Thr Ile
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Phe Thr Lys Ile Pro Thr Ile
1               5

<210> SEQ ID NO 19
<211> LENGTH: 12
<212> TYPE: PRT
<213> ORGANISM: Artificial Sequence
<220> FEATURE:
<223> OTHER INFORMATION: Synthetic peptide

<400> SEQUENCE: 19

Lys Phe Ala Arg Thr Lys Ile Pro Thr Ala Ile Thr
1               5                   10
```

```
<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Phe Ala Arg Thr Glu Ile Pro Thr Ala Ile
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide

<400> SEQUENCE: 21

Lys Phe Ala Arg Thr Glu Ile Pro Thr Ala Ile Thr
1               5                   10
```